(12) United States Patent
Schraga

(10) Patent No.: US 8,934,955 B2
(45) Date of Patent: Jan. 13, 2015

(54) CARTRIDGE WITH LANCETS AND TEST STRIPS AND TESTING DEVICE USING THE CARTRIDGE

(75) Inventor: Steven Schraga, Surfside, FL (US)

(73) Assignee: Stat Medical Devices, Inc., North Miami Beach, FL (US)

( * ) Notice: Subject to any disclaimer, the term of this patent is extended or adjusted under 35 U.S.C. 154(b) by 1045 days.

(21) Appl. No.: 11/035,978

(22) Filed: Jan. 18, 2005

(65) Prior Publication Data

US 2006/0161078 A1 Jul. 20, 2006

(51) Int. Cl.
| | |
|---|---|
| A61B 5/157 | (2006.01) |
| A61B 5/00 | (2006.01) |
| A61B 5/15 | (2006.01) |
| A61B 5/145 | (2006.01) |
| A61B 5/151 | (2006.01) |
| A61M 5/00 | (2006.01) |

(52) U.S. Cl.
CPC ........... *A61B 5/1411* (2013.01); *A61B 5/14532* (2013.01); *A61B 5/15146* (2013.01); *A61B 2562/0295* (2013.01); *A61M 5/008* (2013.01)
USPC ............ 600/347; 600/365; 600/583; 600/584

(58) Field of Classification Search
USPC ........... 600/583, 347, 365, 584; 606/181, 182
See application file for complete search history.

(56) References Cited

U.S. PATENT DOCUMENTS

| | | | |
|---|---|---|---|
| 5,035,704 A | 7/1991 | Lambert et al. | |
| 5,201,324 A | 4/1993 | Swierczek | |
| 5,395,388 A | 3/1995 | Schraga | |
| 5,643,306 A | 7/1997 | Schraga | |
| 5,971,941 A * | 10/1999 | Simons et al. | 600/573 |
| 6,228,100 B1 | 5/2001 | Schraga | |
| 6,506,168 B1 | 1/2003 | Fathallah et al. | |
| 7,299,081 B2 * | 11/2007 | Mace et al. | 600/573 |
| 2003/0083686 A1 * | 5/2003 | Freeman et al. | 606/181 |
| 2004/0092995 A1 * | 5/2004 | Boecker et al. | 600/576 |
| 2004/0230216 A1 * | 11/2004 | Levaughn et al. | 600/583 |
| 2005/0118071 A1 | 6/2005 | Sacherer | |
| 2006/0224172 A1 | 10/2006 | Levaughn et al. | |
| 2012/0220895 A1 | 8/2012 | Vine et al. | |

FOREIGN PATENT DOCUMENTS

WO  WO 2005/018710  3/2005

OTHER PUBLICATIONS

U.S. Appl. No. 11/073,736 in the name of Schraga, filed Mar. 8, 2005.
Chinese Office Action dated Sep. 10, 2010 that issued with respect to patent family member Chinese Patent Application No. 2006-80007541.0.

* cited by examiner

*Primary Examiner* — Lee S Cohen
*Assistant Examiner* — Emily Lloyd
(74) *Attorney, Agent, or Firm* — Greenblum & Bernstein, P.L.C.

(57) ABSTRACT

A cartridge for a testing device and method of testing using the testing device with the cartridge is disclosed. The cartridge includes a plurality of lancet needles, a plurality of test strips, and a mechanism allowing the cartridge to be mounted to the testing device. The method provides for puncturing a surface of skin using the testing device by arranging the testing device against a user's skin, triggering the testing device so that one of the plurality of lancet needles is caused to penetrate the user's skin, placing an amount of blood on one of the plurality of test strips, and rotating the cartridge to another position.

12 Claims, 26 Drawing Sheets

CARTRIDGE WITH LANCETS AND TEST STRIPS AND TESTING DEVICE USING THE CARTRIDGE

BACKGROUND OF THE INVENTION

1. Field of the Invention

The invention relates to a cartridge which combines a plurality of test strips and a plurality of lancets or lancet needles. The invention also relates to a disposable disk-shaped cartridge for a testing device such as glucose meter. The invention further relates to a method of using a testing device such as a blood glucose meter with a removable/replaceable cartridge. In particular, the invention relates to a cartridge having both lancet needles and test strips which may be disposable, i.e., which can be used once and discarded, and/or which utilizes an arrangement which protects a user from contacting his or her skin with the same surface of the skin engaging portion after the device has been triggered and/or fired.

2. Discussion of Background Information

Lancet devices are commonly used to prick the skin of the user so that one or more drops of blood may be extracted for testing. Some users, such as diabetics, for example, may have to test their blood sugar levels several times a day. This may be accomplished by the user using a simple needle. However, this procedure is often problematic for the user since the needle may be difficult to handle. Additionally, many users simply cannot perform the procedure owing to either a fear of needles or because they lack a steady hand. As a result, lancet devices have been developed which allow the user to more easily and reliably perform this procedure.

Known single-use/disposable lancet devices are not sufficiently and/or properly designed to ensure that they cannot be reused. Moreover, such devices generally do not protect a user from coming into contact with body fluids such as blood which may be on the device after the device has been used.

An improved device would allow the user to use the lancet needle only a single time and more reliably and safely prevent reuse of the lancet needle. The device should also ensure that a contaminated surface of the device cannot come into contact with a user after the device is used. Finally, an improved device would utilize a cartridge which is safe to dispose of, is simple in design, and is inexpensive to produce.

SUMMARY OF THE INVENTION

According to one illustrative aspect of the invention there is provided a disposable cartridge for a testing device or glucose meter.

According to another illustrative aspect of the invention there is provided a cartridge for a testing device, wherein the cartridge comprises a plurality of lancet needles, a plurality of test strips, and a mechanism allowing the cartridge to be mounted to the testing device.

The mechanism that may allow the cartridge to be mounted to the testing device comprises an opening. Each of the plurality of lancet needles may be generally radially oriented. Each of the plurality of test strips may be generally radially oriented. Each of the plurality of lancet needles may be movably mounted to a disk-shaped body. Each of the plurality of test strips may be non-movably mounted to a disk-shaped body. The cartridge may comprise a generally circular shape. The cartridge may comprise a generally circular shape having an outer diameter of no greater than about 2 inches. The cartridge may comprise a generally circular shape having a thickness of no greater than about 0.25 inches.

The cartridge may further comprise a plurality of springs, wherein each spring is mounted to one of the plurality of lancet needles. Each of the plurality of lancet needles may comprise a head portion and a needle portion.

The cartridge may further comprise a ring-shaped member, wherein each needle portion is arranged within an opening of the ring-shaped member.

The cartridge may further comprise a ring-shaped member, wherein each needle portion is movably mounted in a radial opening of the ring-shaped member.

The cartridge may further comprise a ring-shaped member, wherein each of the plurality of lancet needles is movably mounted to the ring-shaped member.

Each of the plurality of test strips may be non-movably mounted to a planar disk-shaped body. The planar disk-shaped body may comprise a thickness of less than about 0.10 inches. Each of the plurality of test strips may comprise electrical contacts. Each of the plurality of test strips may be generally radially aligned with the plurality of lancet needles.

The cartridge may further comprise an alignment mechanism allowing the cartridge to be mounted to the testing device in only a single position.

The cartridge may further comprise one of a notch and a groove which ensures that the cartridge is mounted to the testing device in a predetermined position.

The cartridge may further comprise a locking mechanism preventing rotation of the cartridge once the cartridge has rotated in the testing device to a locking position.

The cartridge may further comprise an opening which prevents rotation of the cartridge after the cartridge has rotated in the testing device to a locking position.

The invention also provides a method of puncturing a surface of skin using a testing device comprising the cartridge of the type described above, wherein the method comprises arranging the testing device against a user's skin, triggering the testing device so that one of the plurality of lancet needles is caused to penetrate the user's skin, placing an amount of blood on one of the plurality of test strips, and rotating the cartridge to another position.

According to another illustrative aspect of the invention there is provided a cartridge for a glucose meter, wherein the cartridge comprises a planar disk-shaped body comprising a plurality of radially oriented test strips and a plurality of radially oriented lancet needles, wherein the cartridge is mountable to the glucose meter.

The planar disk-shaped body may comprise a center opening, wherein the plurality of radially oriented lancet needles are movably mounted, and wherein the center opening allows the cartridge to be removably mounted to the glucose meter.

According to another illustrative aspect of the invention there is provided a method of puncturing a surface of skin using a glucose meter which comprises the cartridge of the type described above, wherein the method comprises arranging the glucose meter against a user's skin, triggering the glucose meter so that one of the plurality of lancet needles is caused to penetrate the user's skin, placing an amount of blood on one of the plurality of test strips, and rotating the cartridge to another position.

According to another illustrative aspect of the invention there is provided a testing device comprising a housing and a cartridge comprising a plurality of lancet needles and a plurality of test strips, wherein the cartridge is movably mounted within the housing.

The cartridge may be generally disk-shaped and comprise a center opening which is rotatably mounted about a hub arranged within the housing. The plurality of lancet needles may be movably mounted to a disk-shaped body and the plurality of test strips may be generally radially oriented. The plurality of lancet needles may be generally radially oriented. The cartridge may be removably mounted to the housing. The housing may comprise a door which can be opened to remove the cartridge.

According to another illustrative aspect of the invention there is provided a glucose meter comprising a housing and a cartridge comprising a plurality of lancet needles and a plurality of test strips. The cartridge is movably and removably mounted within the housing. A mechanism retains the cartridge in a rotational position. A device allows a user to rotate the cartridge between a plurality of positions.

The housing may comprise a door which can be opened to remove the cartridge. The mechanism which retains the cartridge in a rotational position may comprise a deflecting member. The device which allows a user to rotate the cartridge between a plurality of positions may comprise a motor. The mechanism which retains the cartridge in a rotational position may comprise a motor.

The glucose meter may further comprise an alignment mechanism allowing the cartridge to be initially mounted within the housing in only a single position.

The glucose meter may further comprise one of a notch and a groove which ensures that the cartridge is mounted to the housing in a predetermined position.

The glucose meter may further comprise a locking mechanism preventing rotation of the cartridge once the cartridge has rotated in the housing to a locking position.

The cartridge may comprise an opening which prevents rotation of the cartridge after the cartridge has rotated in the housing to a locking position.

According to another illustrative aspect of the invention there is provided a method of puncturing a surface of skin using the glucose meter of the type described above, wherein the method comprises arranging the housing against a user's skin, triggering the glucose meter so that one of the plurality of lancet needles is caused to penetrate the user's skin, placing an amount of blood on one of the plurality of test strips, and rotating the cartridge to another position.

The invention also relates to a combination comprising a rotatably mountable cartridge comprising a plurality of lancet needles each comprising a needle portion that is radially oriented and a plurality of test strips each comprising electrical contacts having portions structured and arranged to be exposed to a user's blood drop. A testing device is included and comprises a cartridge receiving area and a testing area visible and accessible from outside the testing device. When the cartridge is installed on the testing device while resting on a horizontal surface, the portions of the electrical contacts exposed to a user's blood drop extend into the testing area and are visible and accessible to a user from a position above the testing device.

In embodiments, each of the plurality of test strips is generally radially oriented.

In embodiments, each of the plurality of lancet needles is movably mounted to a disk-shaped body.

In embodiments, each of the plurality of test strips is non-movably mounted to a disk-shaped body.

In embodiments, the cartridge has an outer diameter of no greater than about 2 inches.

In embodiments, the cartridge has a thickness of no greater than about 0.25 inches.

In embodiments, the combination further comprises a plurality of springs, wherein each spring is mounted to one of the plurality of lancet needles.

In embodiments, each of the plurality of lancet needles comprises a head portion.

In embodiments, the combination further comprises a ring-shaped member arranged on the cartridge, wherein each needle portion is arranged within an opening of the ring-shaped member.

In embodiments, there is provided a method of puncturing a surface of skin using the combination described above, wherein the method comprises placing a finger in the visible and accessible testing area, triggering the testing device so that one of the plurality of lancet needles is caused to penetrate the user's skin and placing an amount of blood on one of the plurality of test strips.

The invention also provides for a testing device comprising a housing and a generally disk-shaped cartridge comprising a plurality of lancet needles and a plurality of test strips. The cartridge is capable of being removably and rotatably mounted within the housing. The housing has a testing area that is visible and accessible to a user such that, when the cartridge is installed in the housing and when the testing device is resting on a horizontal surface, portions of electrical contacts of one of the test strips are exposed to a user's blood drop and extend into the testing area so as to be visible and accessible from a position above the testing device.

The invention also provides for a combination comprising a generally circular cartridge comprising an outer circumference, a plurality of lancet needles each comprising a needle portion that is radially oriented, and a plurality of test strips each comprising electrical contacts having portions structured and arranged to be exposed to a user's blood drop. A testing device is included that comprises a cartridge receiving area and a testing area arranged outside a housing of the testing device. When the cartridge is installed on the testing device while resting on a horizontal surface, at least one of: a portion of the outer circumference extends outside the housing and portions of electrical contacts are exposed, accessible and visible from outside the testing device; and portions of electrical contacts extend into the testing area and are each of accessible to a user and visible from a position above the testing device.

Other exemplary embodiments and advantages of the present invention may be ascertained by reviewing the present disclosure and the accompanying drawing.

BRIEF DESCRIPTION OF THE DRAWINGS

The present invention is further described in the detailed description which follows, in reference to the noted plurality of drawings by way of non-limiting examples of exemplary embodiments of the present invention, in which like reference numerals represent similar parts throughout the several views of the drawings, and wherein.

DETAILED DESCRIPTION OF THE PRESENT INVENTION

Figure 1:
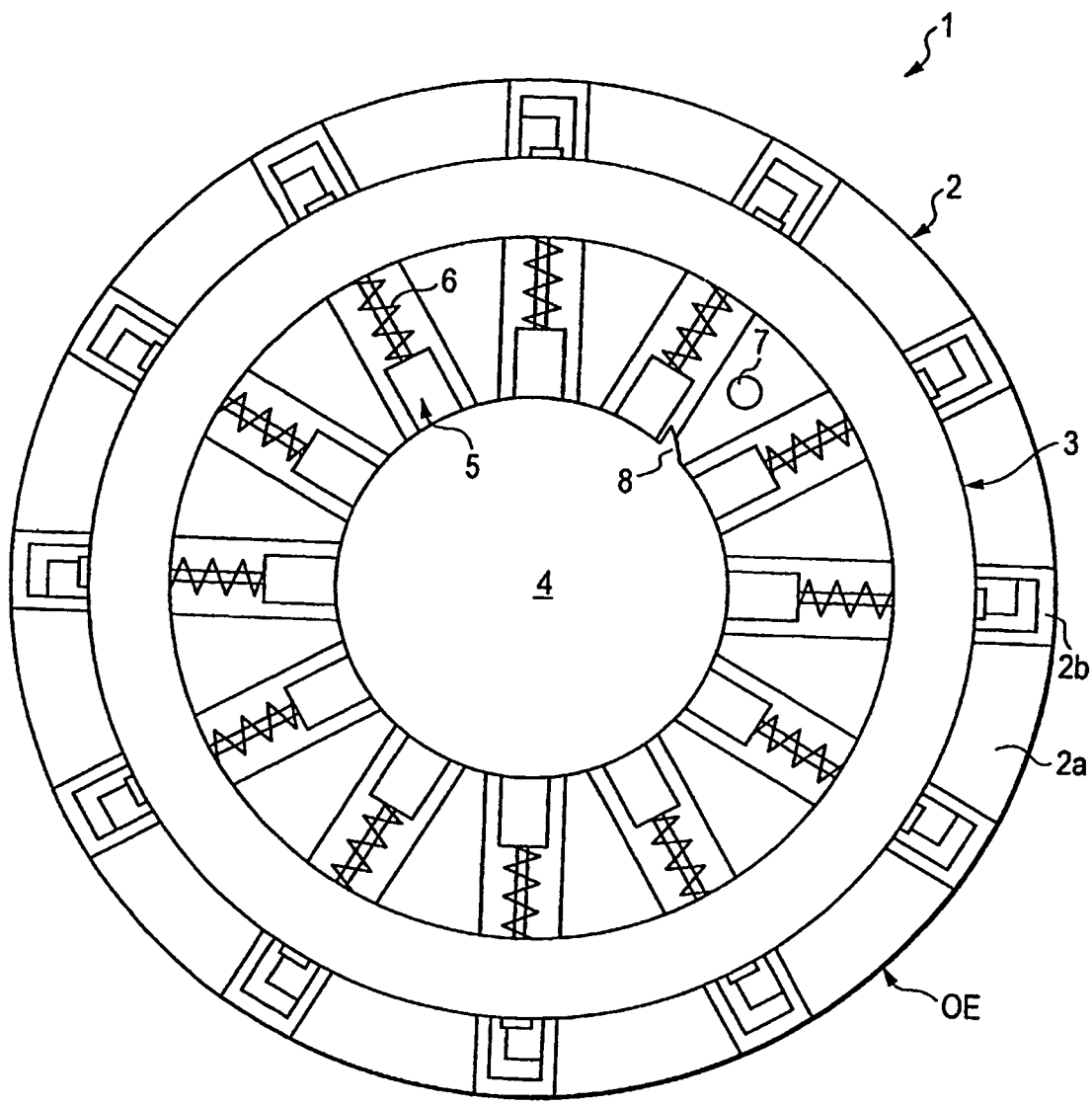
FIG. 1 shows a top view of one embodiment of the cartridge. The contact strips of the test strips extending inwardly from the lancet needle support ring are not shown.

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show structural details of the present invention in more detail than is necessary for the fundamental understanding of the present invention, the description taken with the drawings making apparent to those skilled in the art how the several forms of the present invention may be embodied in practice.

FIGS. 1-8 show a first non-limiting embodiment of a cartridge 1. The cartridge 1 includes a disk-shaped planar body 2 and a lancet needle retaining ring 3. A plurality of lancet needles 5 are mounted to the ring 3 radially. Each lancet needle 5 has a cylindrical needle portion 5*b* and an enlarged head portion 5*a* which can be engaged or contacted by a mechanism which causes the lancet needle 5 to extend beyond the ring 3 (see e.g., FIG. 18). Each lancet needle 5 is movably mounted within a radially oriented opening 3*c* formed in the ring 3. A spring 6 is mounted to each lancet needle 5 in order to ensure that the lancet needle automatically retracts once the lancet needle 5 is caused to move to an extended puncturing position. A plurality of test strips 2*b* are also radially arranged and are generally aligned with the lancet needles 5. By way of non-limiting example, the disk-shaped body 2 can have an outer diameter of between approximately 1.5" and 3" and is preferably approximately 2" in diameter. The cylindrical portion 5*b* of the lancet needles 5 can be made of metal such as stainless steel and can also be of the same material and diameter as conventional lancet needles. The cylindrical head portion 5*a* can have a diameter of approximately 0.15" and can be made of a synthetic resin material which is injection molded onto the cylindrical portion 5*b*. The springs 6 can be of any desired type and can preferably be a wire compression spring. The test strips 2*b* can be in the range of between approximately 0.15" and approximately 0.25" in width, approximately 0.025" and approximately 0.1" in thickness and between approximately 0.5" and approximately 1.25" long.

As can be seen in FIG. 1, the cartridge 1 can utilize a centrally disposed opening 4 which allows the cartridge 1 to be mounted to a mounting arrangement MA (see FIGS. 9-18). Of course, the cartridge 1 can have a variety of designs in order to allow mounting to any number of testing devices. An important aspect of the cartridge 1 relates to the use of a plurality of test strips 2*b* and a plurality of lancet needles 5. In order to ensure that the cartridge 1 is installed in a desired predetermined position of a mounting arrangement MA, the cartridge can include an alignment mechanism 8. This alignment mechanism 8 can have the form of a notch which slides over a projection of the mounting arrangement thereby ensuring that the cartridge 1 can only be installed when oriented in a single angular position. In order to ensure that the cartridge 1 will rotate or index in only a single time, i.e., only 360 degrees, the cartridge 1 can include a locking mechanism 7. This locking mechanism 7 can have the form of an opening within which a pin 101 of the mounting arrangement MA extends when the cartridge 1 rotates a fully 360 degrees from an originally installed position. Once the pin 101 engages the opening 7, the user will know that the cartridge 1 has been fully used, i.e., the user will be able to discern that all of the test strips 2*b* and lancet needles 5 have been used once and that it is time to remove the cartridge 1, discard it, and replace it with a fresh cartridge 1. In order to remove the cartridge 1, the user can simply lift the cartridge 1 out of the mounting arrangement MA slightly, rotate it counter-clockwise one indexing position until the notch 8 is aligned with the projection 108, and then lift it completely out of the mounting arrangement MA. This removal process can also be facilitated by the user pressing down, using either a tool or a finger, on the pin 101 which is biased upwards by a spring.

Figure 2:
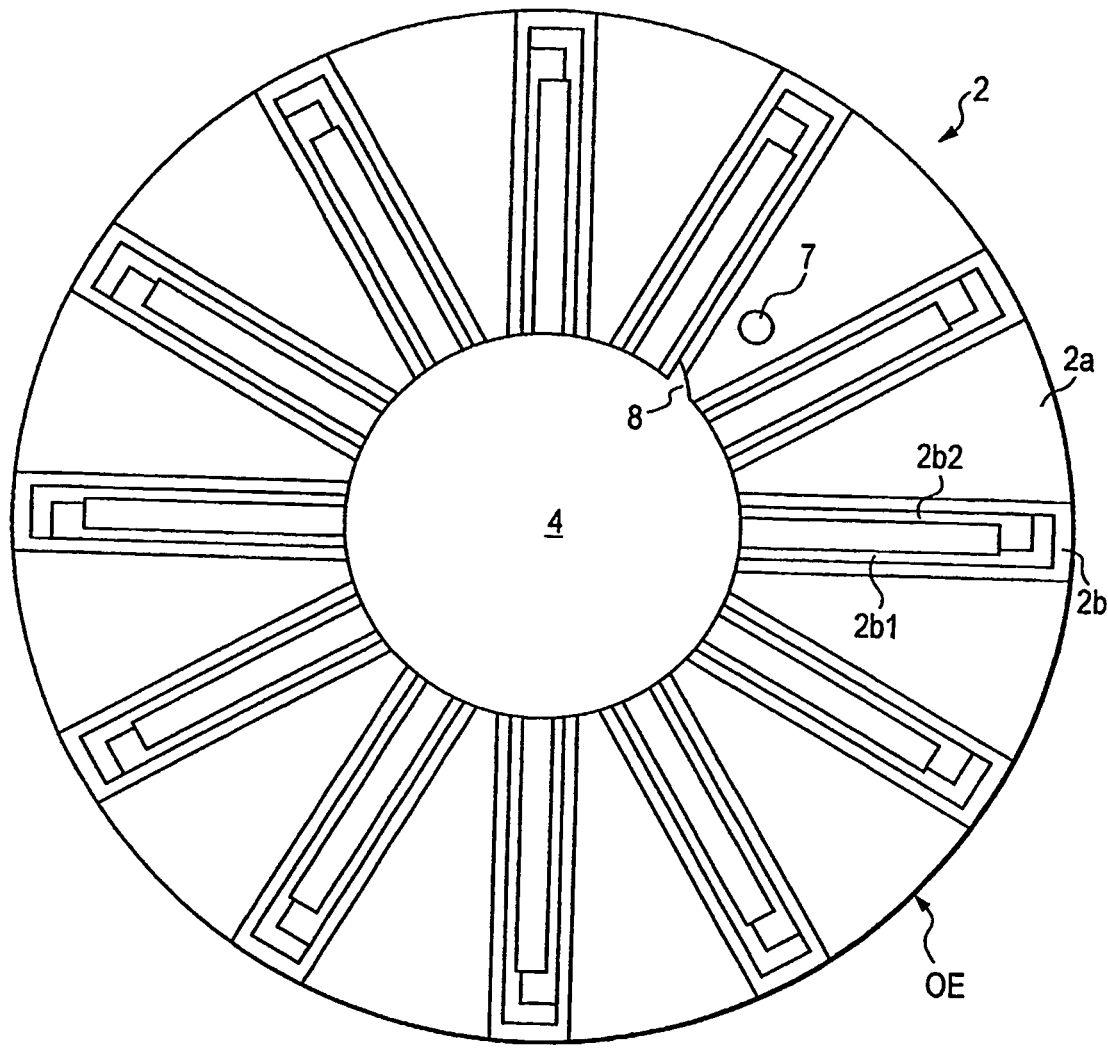
FIG. 2 shows a top view of the cartridge of FIG. 1 with the lancet needle support ring and the lancet needles removed therefrom.
Figure 3:
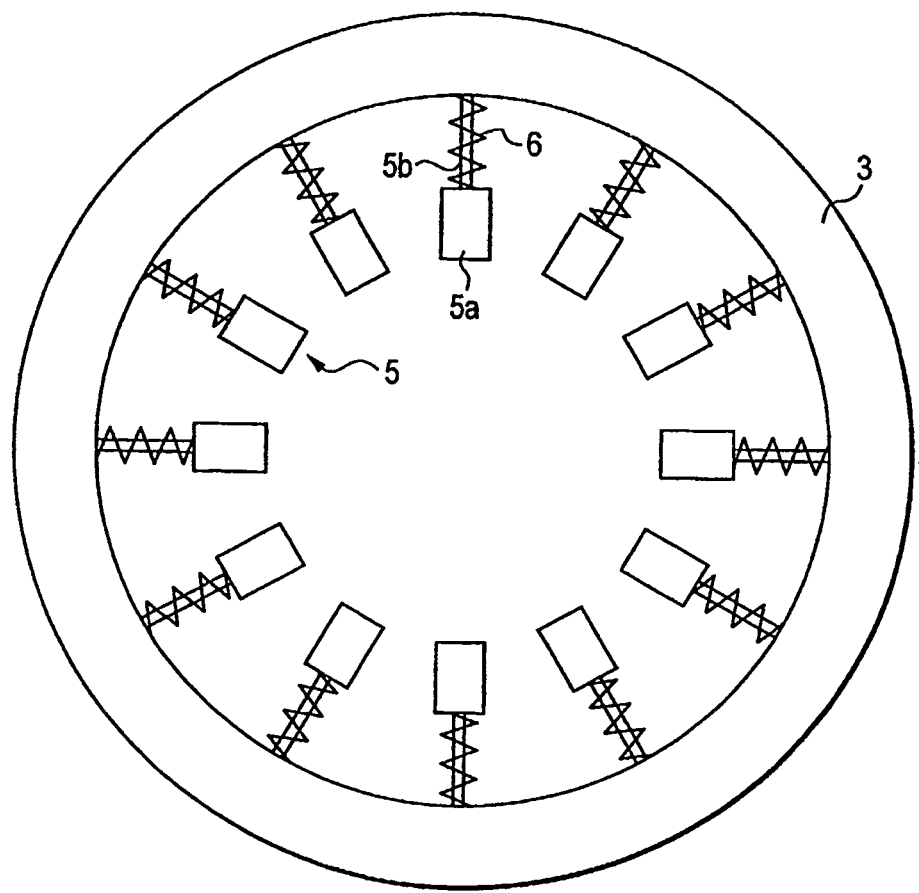
FIG. 3 shows a top view of the lancet needle support ring and the lancet needles used in the embodiment of FIG. 1.
Figure 4:
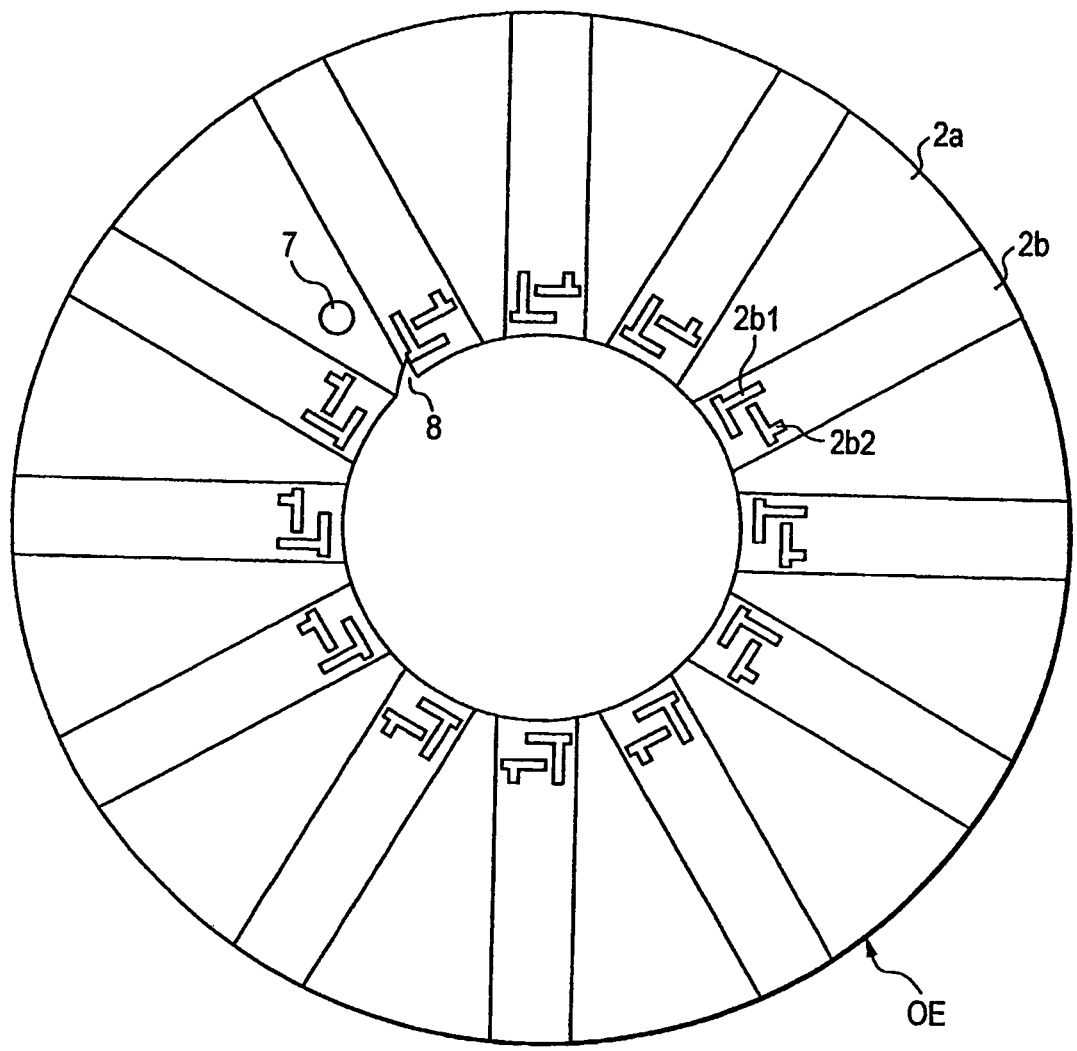
FIG. 4 shows a bottom view of the cartridge of FIG. 1.
Figure 5A:
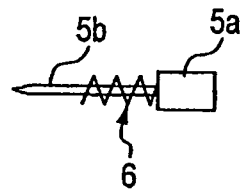
FIG. 5*a* shows a left side view of one of the lancet needles used in the cartridge embodiment shown in FIG. 1. A coil spring is mounted to the needle portion of the lancet needle.
Figure 5B:
FIG. 5*b* shows an end view of the lancet needle of FIG. 5*a*.
Figure 5C:
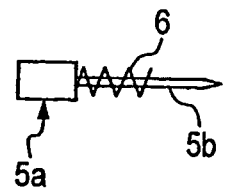
FIG. 5*c* shows a right side view of the lancet needle shown in FIG. 5*a*.
Figure 6:
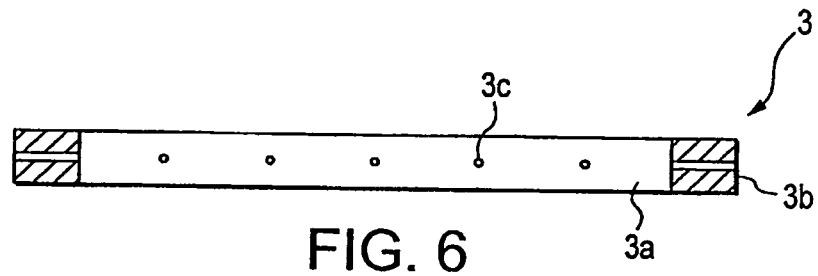
FIG. 6 shows a cross-section view of the lancet needle holding ring shown in FIG. 3. The lancet needles and springs have been removed.
Figure 7:
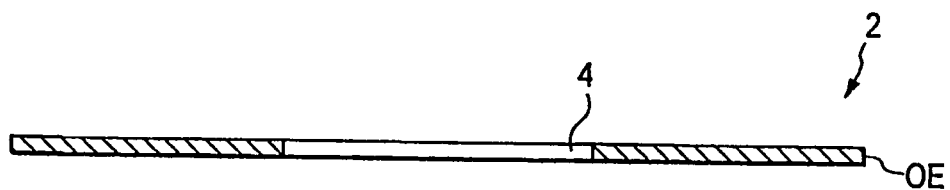
FIG. 7 shows a cross-section view of the disk-shaped body containing the test strips shown in FIG. 2.
Figure 8:
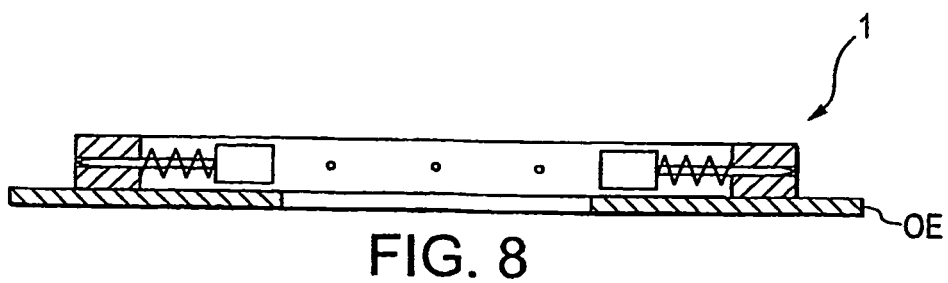
FIG. 8 shows a cross-section view of the cartridge shown in FIG. 1. For the sake of clarity, only the lancet needles positioned at three o'clock and nine o'clock are shown installed on the cartridge. The lancet needles and the springs are not shown in cross-section.
Figure 9:
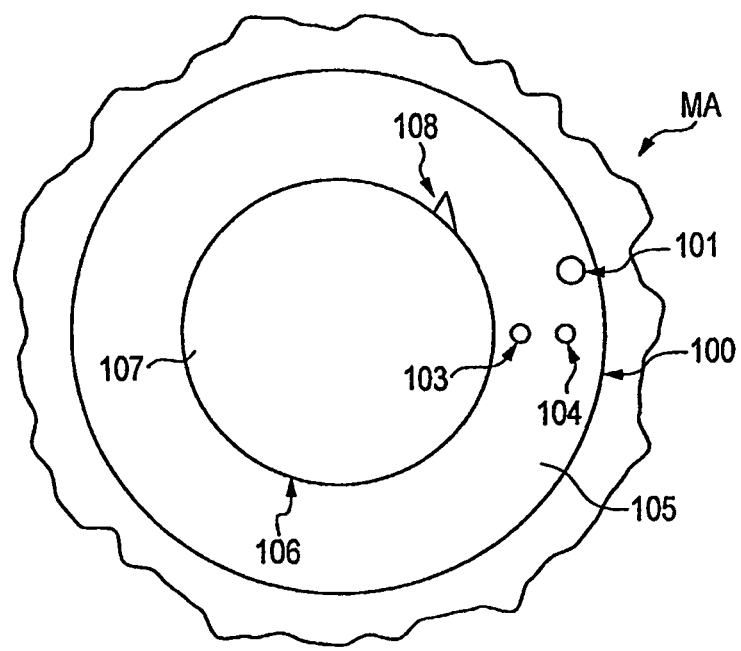
FIG. 9 shows a top view of one embodiment of a mounting arrangement which can be used to mount the cartridge of FIG. 1 in a testing device.
Figure 10:
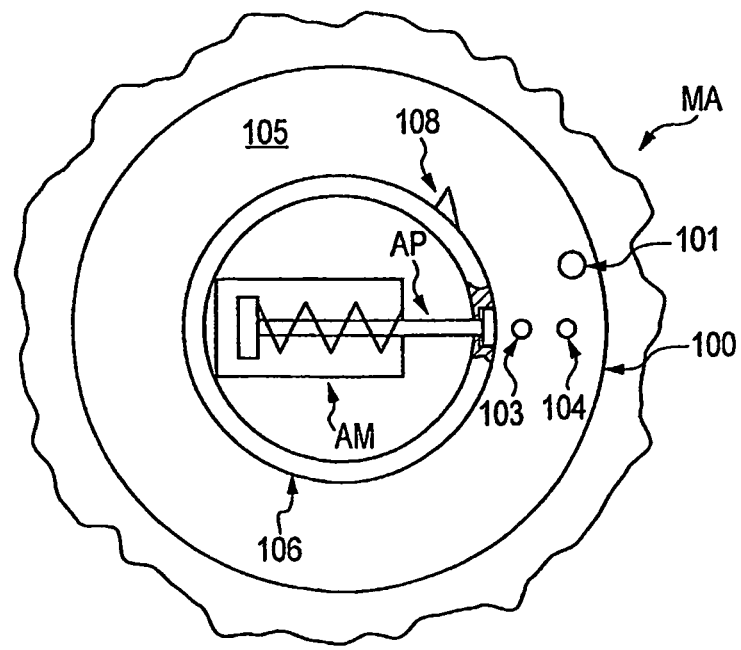
FIG. 10 shows a top view of the mounting arrangement of FIG. 9 with a hub cover removed to expose an electrical actuating mechanism which is used to move each lancet needle to an extended puncturing position.
Figure 11:
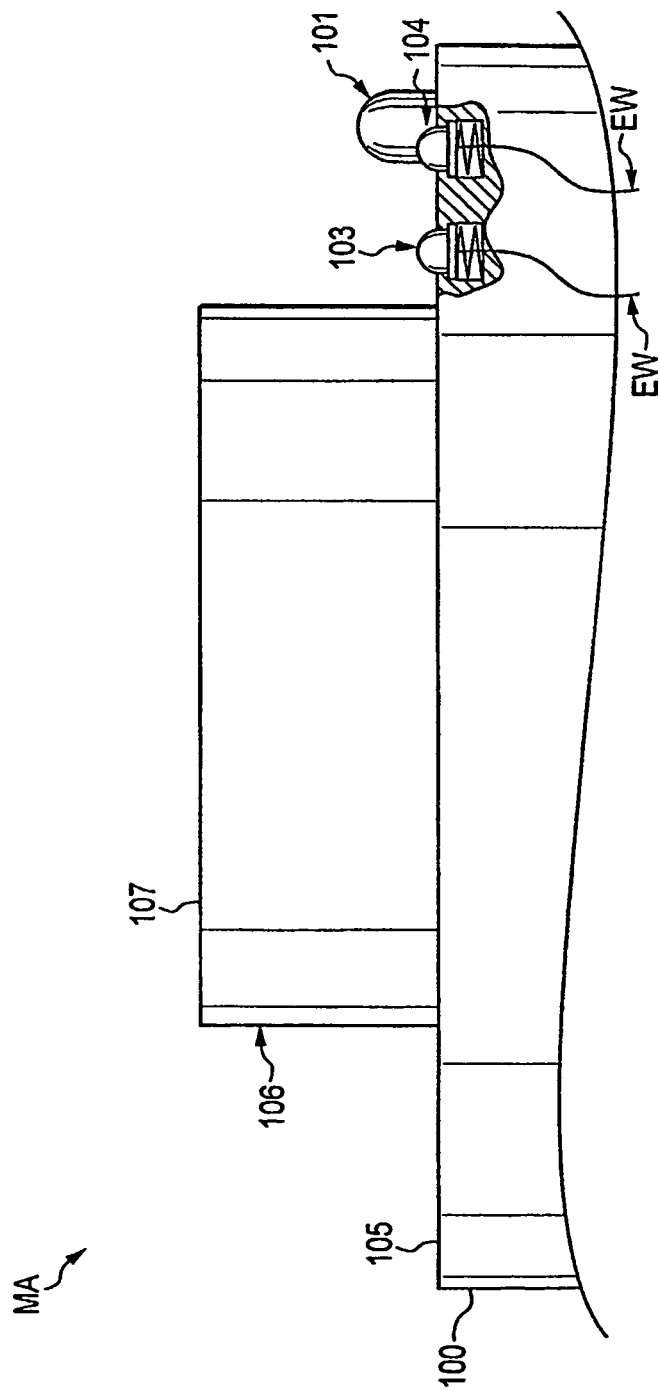
FIG. 11 shows a side view of the mounting arrangement of FIG. 9.
Figure 12:
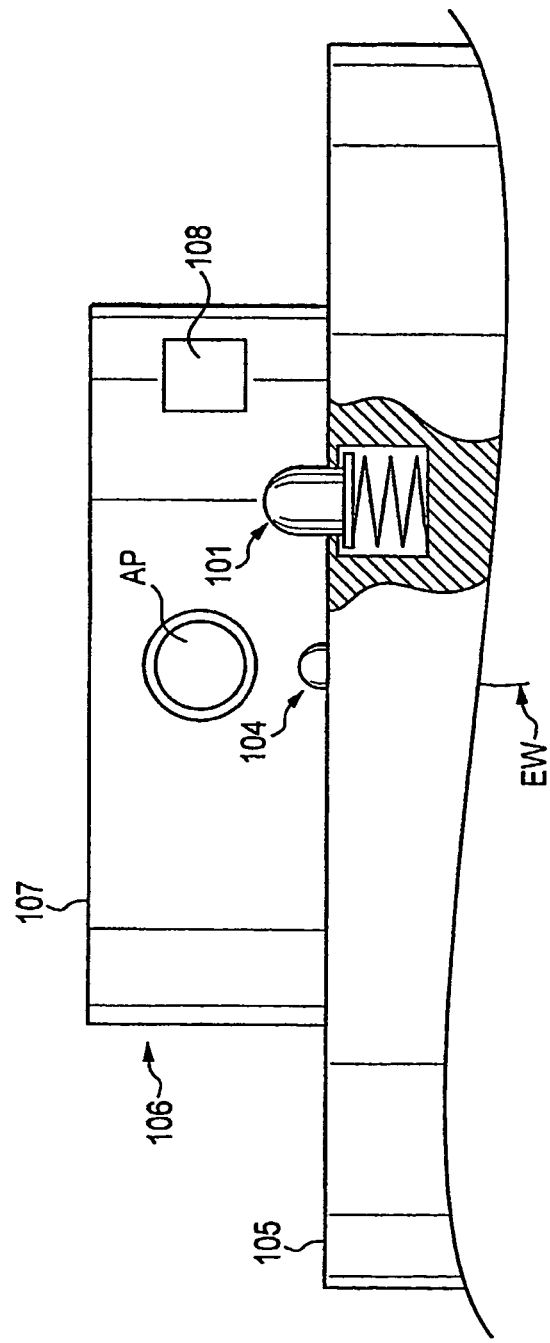
FIG. 12 shows a side view of the mounting arrangement of FIG. 11. The side view is of the mounting arrangement rotated from the three o'clock position of FIG. 11 to the six o'clock position shown in FIG. 12.
Figure 13:
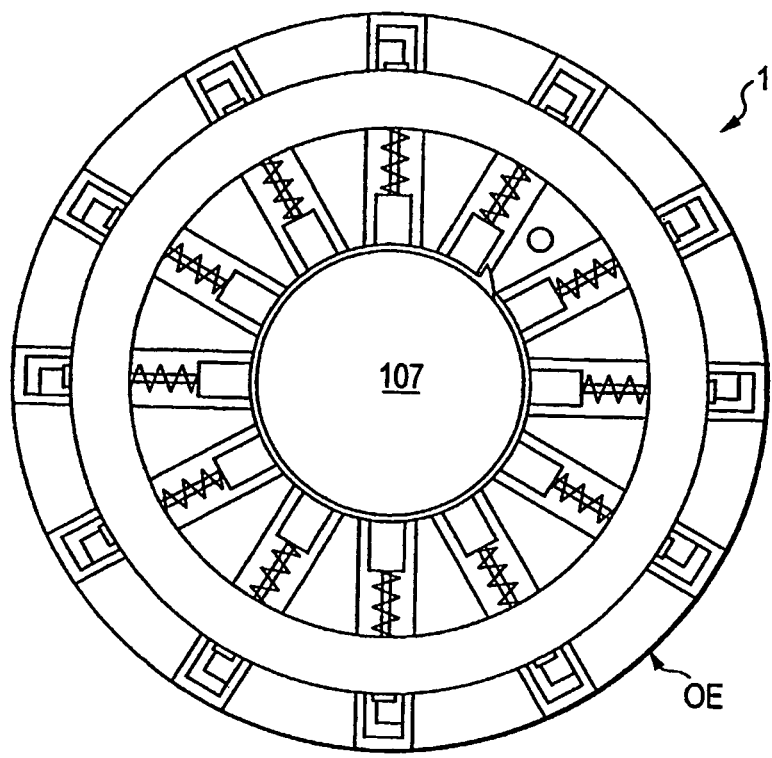
FIG. 13 shows a top view of the cartridge of FIG. 1 installed on the mounting arrangement of FIGS. 9-12.
Figure 14:
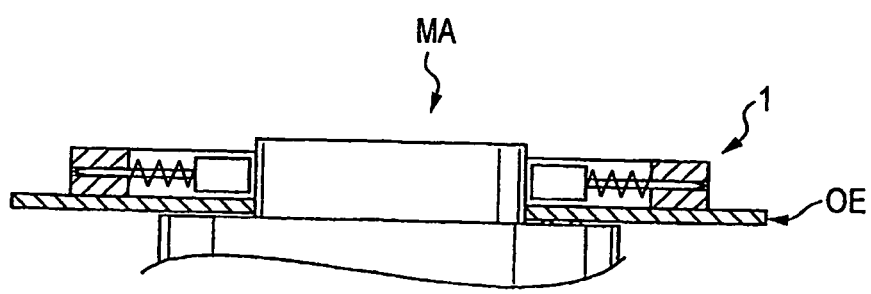
FIG. 14 shows a side cross-section view of FIG. 13. The cartridge of FIG. 8 is shown installed on the mounting arrangement of FIG. 11.
Figure 15:
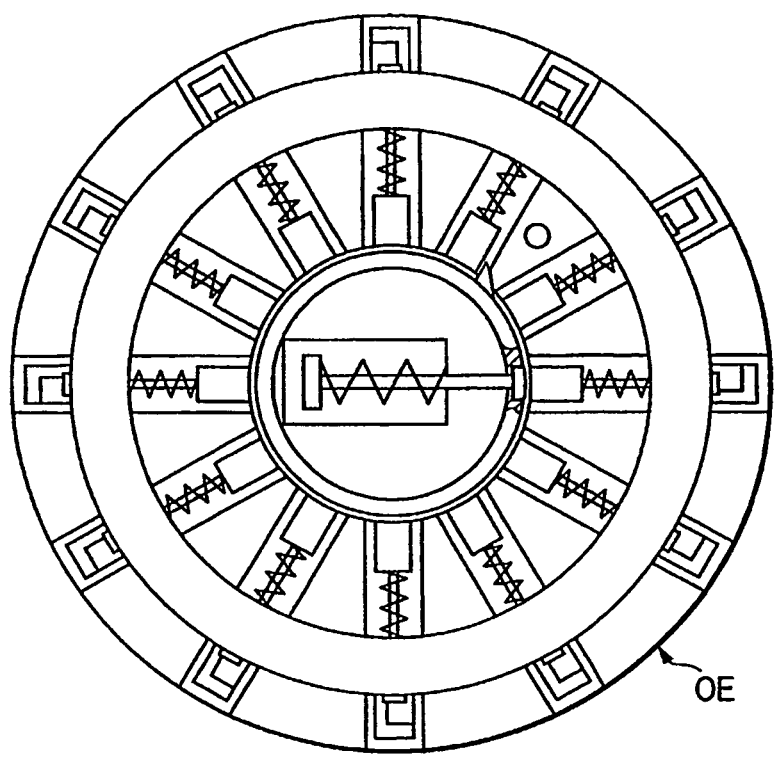
FIG. 15 shows a top view of the cartridge of FIG. 1 installed on the mounting arrangement of FIG. 10. The actuating plunger is shown in a retracted position prior to the testing device being triggered.
Figure 16:
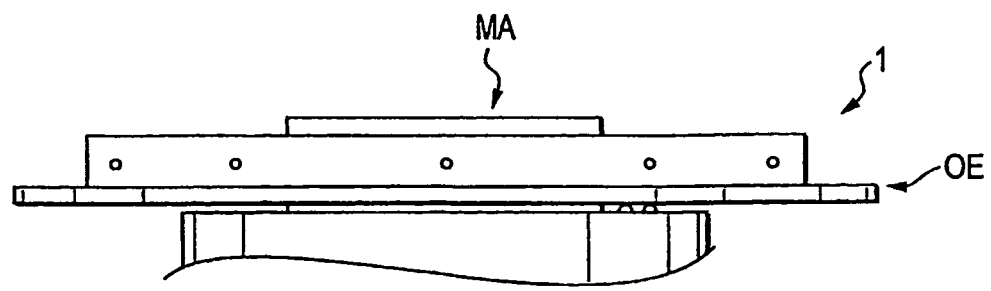
FIG. 16 shows a side view of FIG. 15.

As can be seen in FIGS. 2 and 4, the test strips 2*b* include electrical contacts 2*b*1 and 2*b*2. In the upper surface of the body 2, the contacts are exposed to a blood drop of the user in an area adjacent the outer circumferential edge OE of the body 2. The arrangement of contacts on a test strip which will receive a blood drop is, of course, conventional. The contacts 2*b*1 and 2*b*2 extend along the test strip 2*b* and are electrically connected to contact pads or surfaces arranged on a lower surface of the body 2. These contact pads are positioned to ensure that they provide electrical contact with contacts 103 and 104 of the mounting arrangement MA. As the contacts 103 and 104 are positioned in only a single location, i.e., at 3 o'clock (see FIGS. 9-11) on the mounting arrangement MA, an electrical connection is established between a testing device and each test strip 2*b* only when the test strip 2*b* is located in a predetermined position and/or triggering position.

As can be seen in FIGS. 5*a*-8, the cartridge 1 is simple in design and construction and includes only four main parts, i.e., the body 2, the ring 3, the needles 5 and the springs 6. The ring 3 can be a synthetic resin material member having an inner circumferential surface 3*a* and an outer circumferential surface 3*b* and can be made by injection molding and thereafter provided with the openings 3*c* by, e.g., drilling. Alternatively, the ring 3 can be made by securing together two pieces each having half-openings formed therein. The ring 3 can be secured to the body 2 by any number of techniques such as bonding, ultrasonic welding, fasteners, snap connections, etc. Although the ring 3 is shown having a generally rectangular cross-section, the invention also contemplates a ring 3 having a square cross-section as well as other shapes. The equally spaced openings 3*c* are, of course, made to be slightly larger in diameter than the cylindrical portions 5*b* so that the lancet needles 5 are capable of sliding freely within the openings 3*c*.

FIGS. 9-12 illustrate one non-limiting mounting arrangement MA by which one can mount the cartridge 1 to a testing device such as a glucose meter. The mounting arrangement MA can utilize a cartridge support surface 105 which is coupled to and/or formed integrally with a wall 100 of the testing device or the housing thereof. A hub member 106 extends from the support surface 105. A cover 107 covers the hub 106. The hub 106 can be generally circular and can have an outer diameter which is slightly smaller than the central opening 4 of the cartridge 1. An actuating mechanism AM is arranged within the hub 106. The actuating mechanism AM is designed to engage one of the lancet needles 5 when the cartridge 1 is located in one of a number of predetermined positions. In this regard, the actuating mechanism AM can have the form of a solenoid wherein an electrically actuated plunger AP is caused to extend out from the hub 106 rapidly when the solenoid is electrically energized. The solenoid includes a spring for automatically retracting the plunger AP. The solenoid is designed so that the plunger AP is expanded and retracted quickly, i.e., in a fraction of a second, so that the lancet needle 5 can also expand and retract quickly. Although not shown, the solenoid can be electrically connected to the processor circuit of the testing device via wires and/or other types of electrical connections. Of course, the invention contemplates non-electrical and/or mechanical devices for causing the lancet needles 5 to move to the extended position.

As explained above, the mounting arrangement MA includes an alignment projection 108 which extends from the outer cylindrical surface of the hub 106. The projection 108 has a triangular shape which corresponds to the shape of the notch 8 of the cartridge 1. Two spring biased electrical contact pins 103 and 104 extend from the support surface 105. As explained above, these pins 103 and 104 provide electrical contact with the contacts 2b1 and 2b2 of each test strip 2b when the test strip 2b is located above the contacts 103 and 104. Although not shown, the contact pins 103 and 104 are connected to the processor of the testing device via wires EW or other electrical connections. A spring biased locking pin 101 also extends from the support surface 105. As explained above, this pin 101 engages the lower surface of the cartridge 1 until the opening 7 moves directly over the pin 101 wherein the pin 101 then protrudes into the opening 7 so as to prevent further rotational movement of the cartridge 1.

FIGS. 13-16 show the cartridge 1 mounted to the mounting arrangement MA. In this position, the notch 8 is aligned with the projection 108 and the lancet needles 5 are all in the retracted position.

Figure 17:
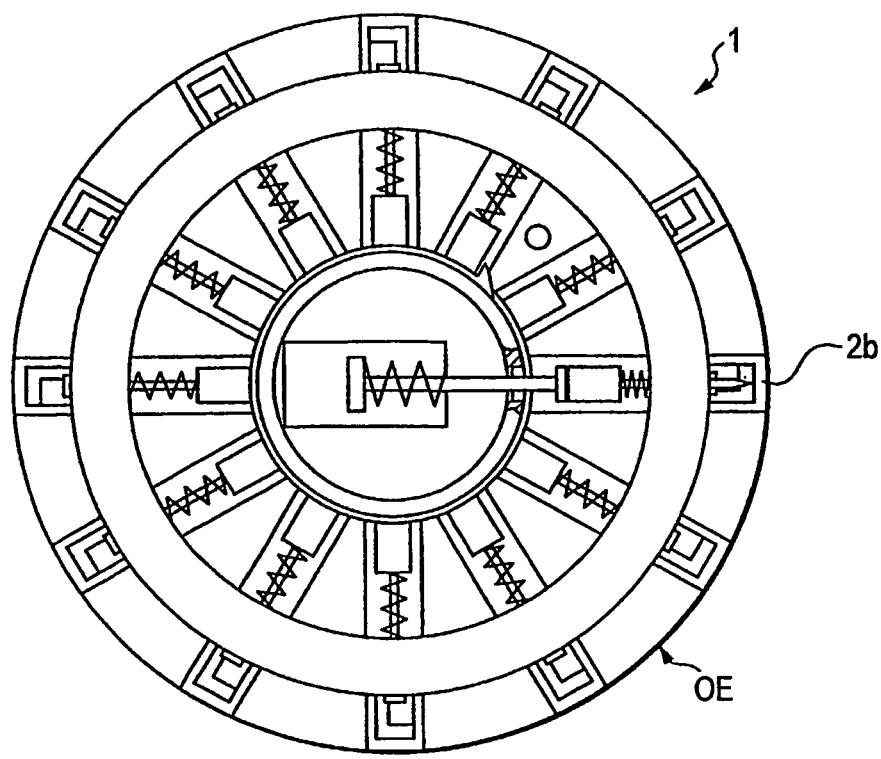
FIG. 17 shows a top view similar to that of FIG. 15 with the actuating plunger being shown in an extended position after the testing device is triggered.
Figure 18:
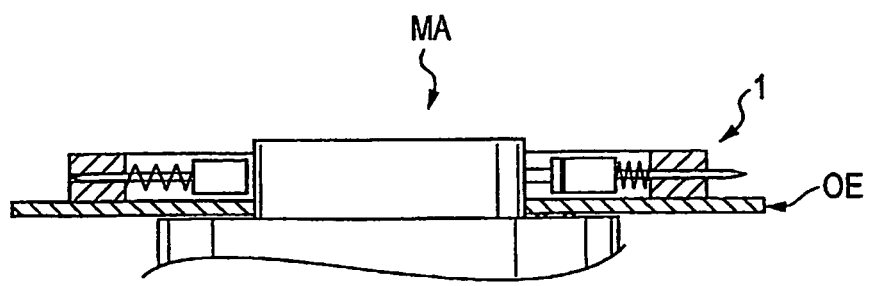
FIG. 18 shows a side cross-section view of FIG. 17.
Figure 19:
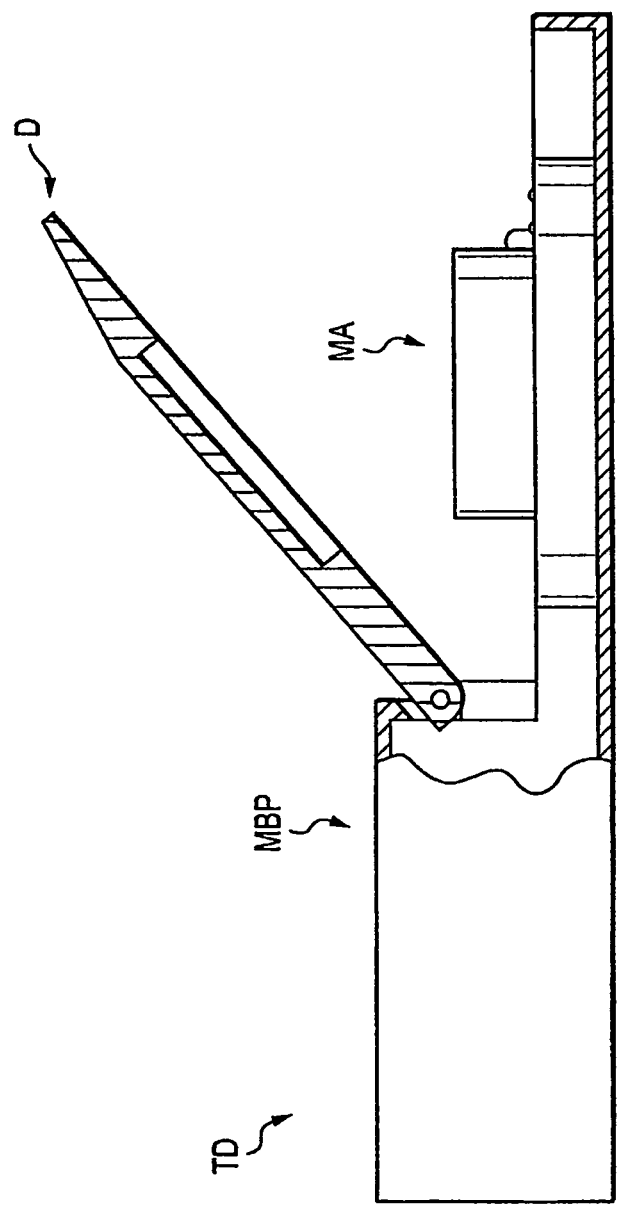
FIG. 19 shows a side view of a testing device which includes the mounting arrangement of FIGS. 9-12. The testing device is shown with a door in an open position and ready to receive the cartridge.
Figure 20:
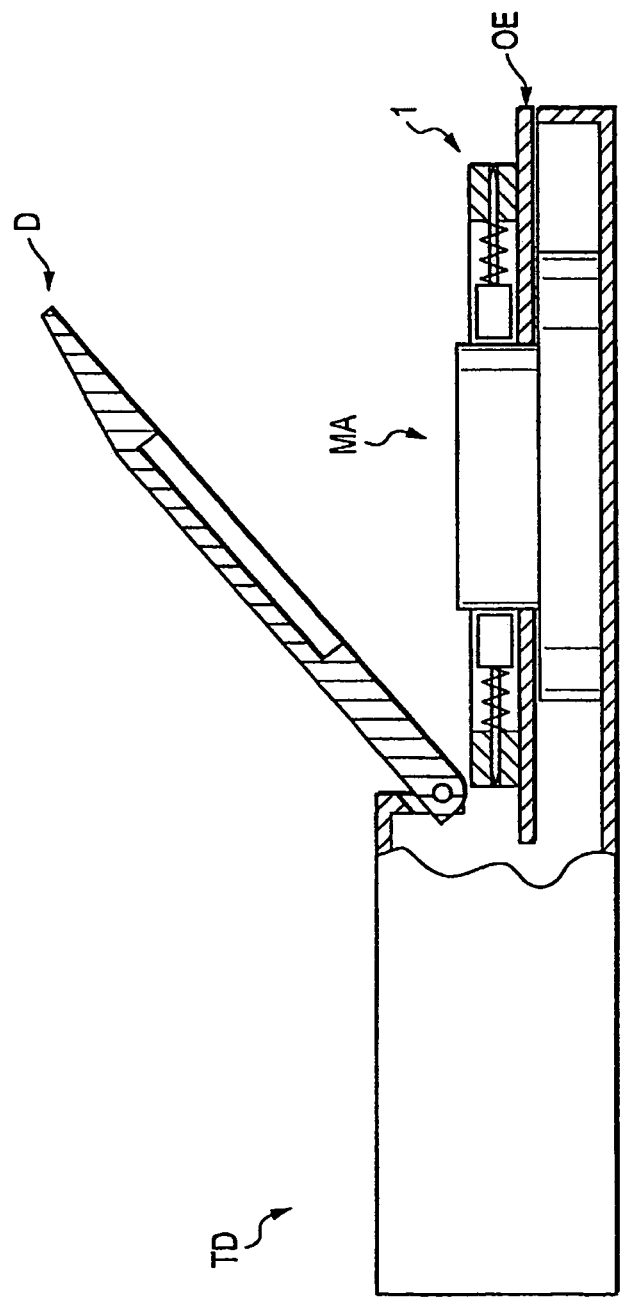
FIG. 20 shows a side view of the testing device of FIG. 19 with the cartridge of FIG. 1 installed therein.
Figure 21:
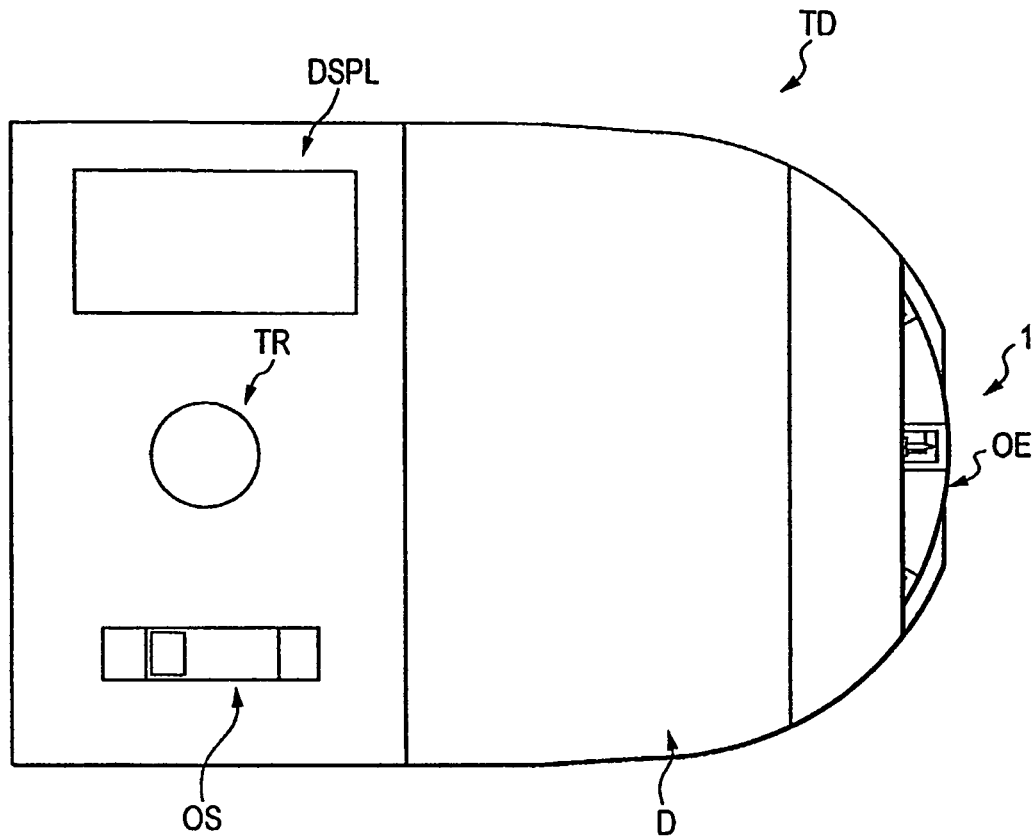
FIG. 21 shows a top view of the testing device of FIG. 22. The test device includes, among other things typically utilized on a test device or glucose meter, a display, a trigger and an on-off switch.

FIGS. 17 and 18 show what happens to the lancet needle 5 at the 3 o'clock position when the solenoid or actuating member AM is activated. As can be seen, the lancet needle 5 extends beyond an outer circumferential surface of the ring 3. This occurs forcing the lancet needle 5 radially outwardly against the biasing force of the spring 6. In this position, the needle would puncture a user's finger (see e.g., FIG. 22). Once retracted, the user can simply rotate the finger so that a drop of blood is placed onto the contacts of the test strip 2b which is positioned directly beneath the needle 5. Moreover, because the test strip 2b is positioned over the contacts 103 and 104, the user will be able to determine a blood testing result from the testing device by placing a drop of blood onto the test strip 2b. The particular way in which the testing device or glucose meter determines the blood testing result from a blood sample placed on a test strip is conventional and is not discussed in detail herein.

Figure 22:
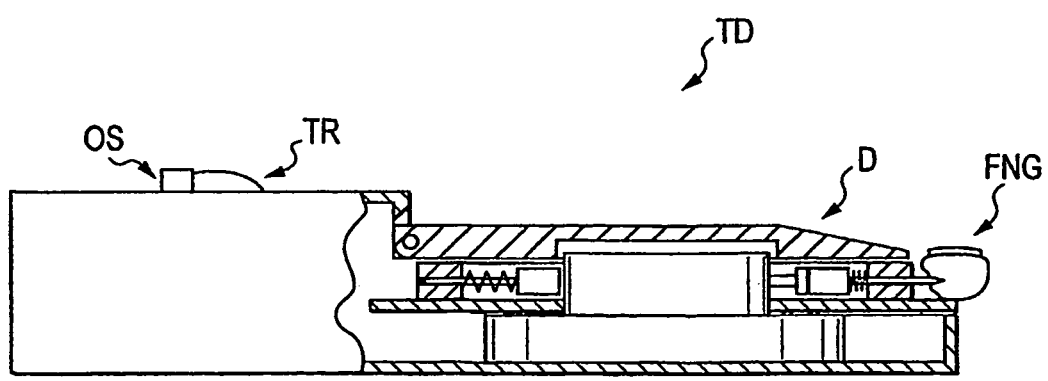
FIG. 22 shows a side view of the testing device of FIG. 20 with the door shown in a closed position. A finger is shown being punctured by one of the lancet needles after the test device has been triggered.

FIGS. 19-22 shows one non-limiting testing device TD and/or a housing thereof which can utilize the mounting arrangement MA. In this embodiment, the testing device TD utilizes a main body portion MBP and a cartridge receiving portion which includes the mounting arrangement and a door D which can be opened and closed to allow a user to remove the cartridge 1. In this embodiment, the door D is hinged or pivotally mounted to the main body portion MBP. Of course, the invention contemplates other ways of mounting the door D. Although not shown, the main body portion MBP can include all of the features conventionally used on glucose meters such as a processor, battery, display DSPL, input keys, a trigger TR, an on/off switch OS, as well as other electronic components. FIG. 22 illustrates one way in which the testing device can be used to puncture a user's finger FNG. Once punctured, the user can rotate and/or manipulate the finger FNG to place a blood drop onto the contacts of the test strip 2b to enable the testing device to provide a result. The way in which the result is produced in a testing device, such as a glucose meter, by placing a drop of blood on a test strip is, of course, conventionally known and will not be described in detail herein. By way of non-limiting example, the user can rotate the cartridge 1 between the various counter-clockwise positions by manually engaging the outer edge OE with a finger. In this regard, the outer edge OE can be provided with a high-friction surface. This high friction edge can take the form of e.g., a silicone rubber layer or a knurled or grooved edge.

Figure 23:
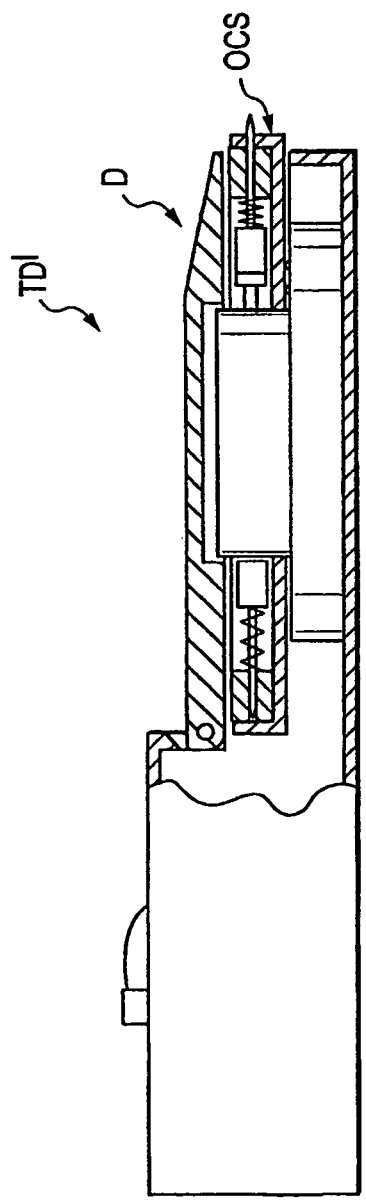
FIG. 23 shows a side view of another embodiment of a testing device. The testing device is shown with the door in a closed position and includes the mounting arrangement and a second embodiment of a cartridge shown in FIG. 24. One of the lancet needles is shown in the extended position after the test device has been triggered.
Figure 25:
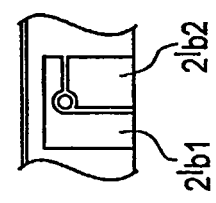
FIG. 25 shows a partial side view of the outer surface of the annular rim showing the test strip contacts and the opening through which passes one of the lancet needles.
Figure 24:
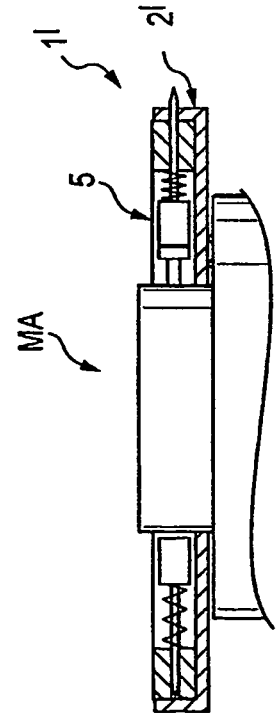
FIG. 24 shows a side view of the mounting arrangement of FIGS. 9-12 with a second embodiment of a cartridge. The cartridge is similar to that shown in FIG. 1 except that an outer circular edge has been bent or oriented upwards at a right angle forming an annular and/or cylindrical rim. Moreover, in this cartridge, unlike the cartridge of FIG. 1, the electrical contacts which receive the blood drop for testing are arranged on an outer surface of the test strip body, and include openings which allow the lancet needles to pass through the annular rim. One of the lancet needles is shown in the extended position after being triggered.

FIGS. 23-25 show a side view of another embodiment of a testing device TD'. The testing device TD' is similar to that of FIGS. 19-22 and utilizes a door D. However, this embodiment of the testing device TD' is designed to function with a second embodiment of a cartridge 1'. The cartridge 1' is shown in FIG. 24 mounted to the mounting arrangement MA. As is shown in FIG. 24, the cartridge 1' is designed so that the lancet needles 5 extend through the test strips. In this regard, FIG. 24 shows one of the lancet needles 5 in the extended position after the test device has been triggered. The cartridge 1' is similar to the first embodiment shown in FIG. 1 except that an outer circular edge has been bent or oriented upwards at a right angle thereby forming an annular and/or cylindrical rim. Moreover, in this cartridge 1', unlike the cartridge of FIG. 1, the portion of electrical contacts which receive the blood drop for testing are arranged on an outer cylindrical surface OCS of the test strip body. As a result, the outer ends of the test strips include an opening (see FIG. 25) which allows the lancet needle 5 to pass through the annular rim. As can be seen in FIG. 25, the contact portions 2'b1 and 2'b2 are spaced slightly from the opening to ensure that the needle does not form an electrical connection between the contact portions 2'b1 and 2'b2 when it moves to the extended position shown in FIG. 24. Although the cartridge 1' embodiment shown in FIGS. 23 and 24 utilizes a lancet retaining ring 3 of the type used in the cartridge 1 shown in FIG. 1, the invention contemplates a cartridge body 2' which does not utilize the ring 3. Instead, at least the cylindrical end portion of the body is made sufficiently thick to perform the needle retaining function of the ring 3. Alternatively, as is contemplated with any of the cartridge embodiments disclosed herein, the ring 3 and body 2 (and more specifically the ring 3 and portions 2a) can be formed as a one-piece member. With reference to FIG. 23, it can be seen that the testing device TD' would function as follows: once a user places a skin surface against the outer cylindrical surface OCS, the device can be triggered to cause the lancet needle 5 to move quickly to the extended position (see FIG. 23) and back to a rest or initial position. If the user then allows the skin surface to remain positioned against the surface OCS, the contacts 2'b1 and 2'b2 will be able to receive the blood which exits from the puncture. The testing device TD' can thus provide a result more quickly since it does not require the user to significantly reposition the skin surface to obtain the blood sample.

Figure 26:
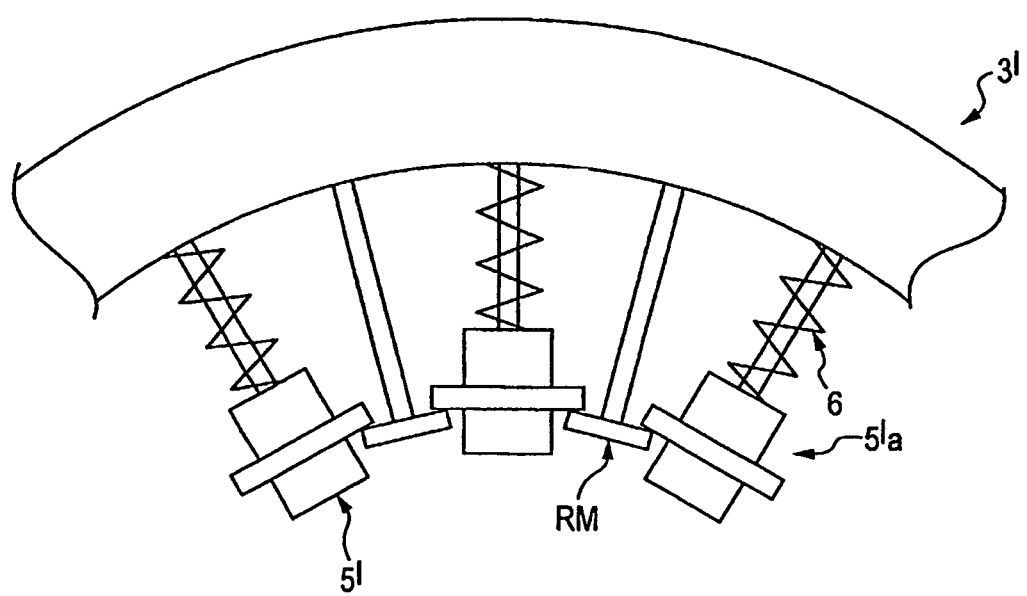
FIG. 26 shows a partial top view of another embodiment of an assembly including a lancet needle holding ring and lancet needles. This arrangement provides for a plurality of radially oriented retaining members which ensure that the lancet needles remain mounted to the lancet needle holding ring. The assembly can be used on the cartridge shown in FIG. 1 in place the assembly shown in FIG. 3.

FIG. 26 illustrates another embodiment of a lancet needle holding ring 3' and needles 5' which can be used on any of the cartridges disclosed herein. The ring 3' is similar to ring 3 shown in FIG. 3 except that it also includes a plurality of lancet needle retaining members RM. The retaining members RM are generally radially arranged and are equally angularly spaced. Each retaining member RM has one end coupled to an inner cylindrical surface of the ring 3' and a head portion which engages with portion of a flange of the head 5'a of the lancet needles 5'. This arrangement thus provides for a plurality of radially oriented retaining members RM which ensure that the lancet needles 5' remain mounted to the lancet needle holding ring 3' when the cartridge is removed from the testing device. The retaining members RM can be integrally formed with the ring 3' and can be deflectable so that the lancet needles 5' can be installed on the ring 3' more easily. Of course, this ring 3' and needle 5' arrangement can be used on any of the cartridge embodiments disclosed herein.

Figure 27:
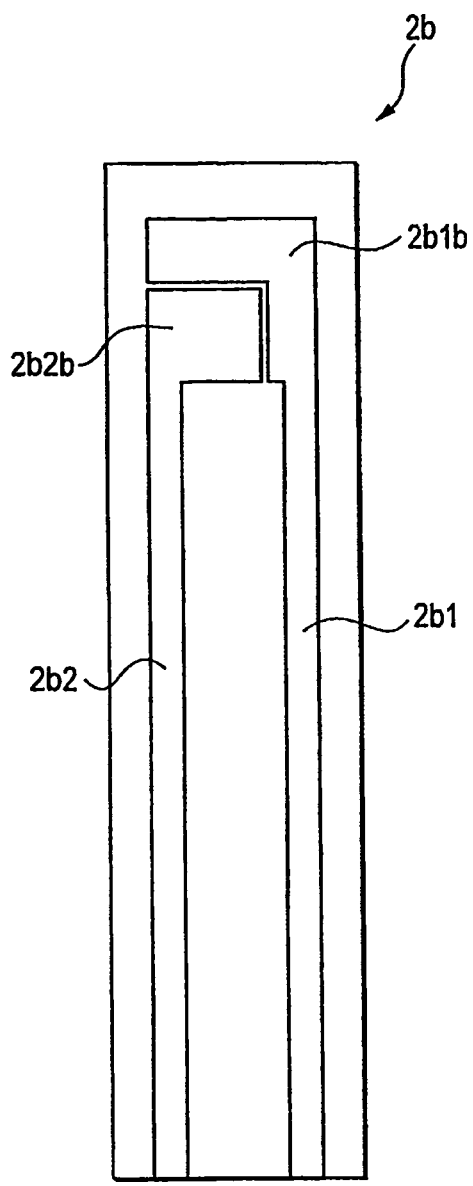
FIG. 27 shows a front or top view of one of the test strips used on the cartridge of FIG. 1.
Figure 28:
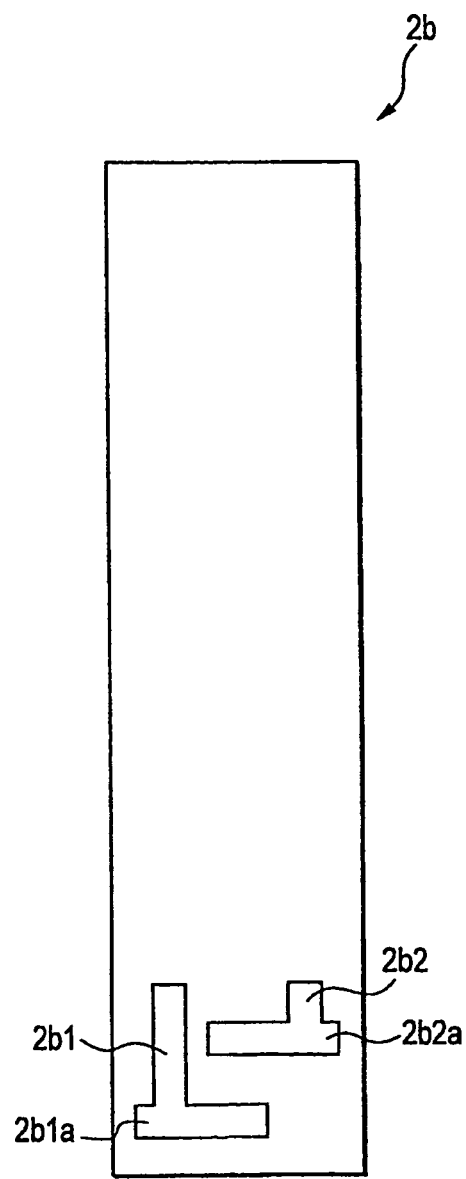
FIG. 28 shows a rear or bottom view the test strip shown in FIG. 27.

FIGS. 27 and 28 shows a front and rear views of one non-limiting embodiment of the test strip 2b which can be used on any of the cartridges disclosed herein. Of course, the invention contemplates utilizing conventional test strips provided they are configured for use on a cartridge of the type disclosed herein. The test strip 2b utilizes contacts and/or electrodes of the type which are known in the art. However, in the instant embodiment, the test strip 2b should utilize contact sections 2b2b and 2b1b which are configured to receive thereon a sample of blood or other body fluid. These sections 2b2b and 2b1b are electrically connected to rear facing contact pads 2b2a and 2b1a via electrode sections 2b2 and 2b1. The contact pads 2b2a and 2b1a are located in a position on the test strips 2b so that each contact pad makes electrical contact with the pin contacts 103 and 104 when a particular test strip 2b is moved to a needle triggering position, e.g., the 3 o'clock position shown in FIGS. 17 and 18.

Figure 29:
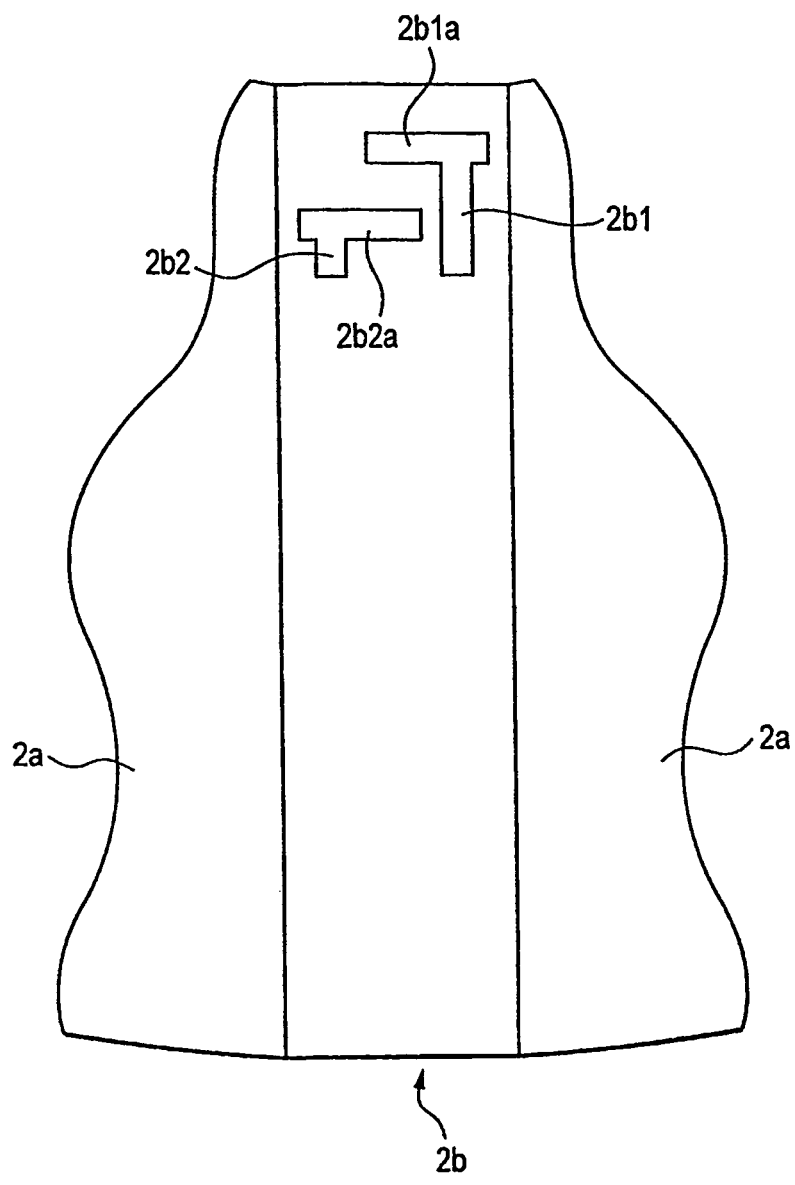
FIG. 29 shows a partial enlarged view of FIG. 4.
Figure 30:
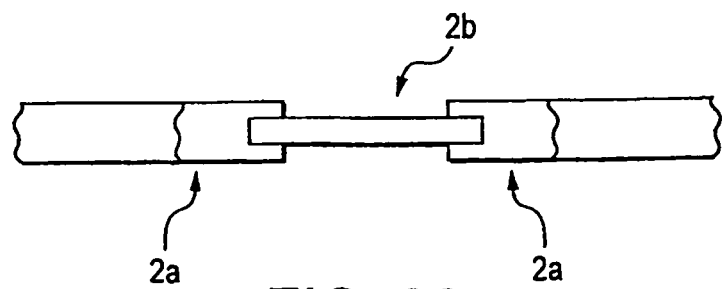
FIG. 30 shows an end view of FIG. 29.

FIGS. 29 and 30 illustrate one non-limiting way in which each of the test strips 2b can be connected to and/or arranged on the planar disk body 2. According to this embodiment, each test strip 2b is fitted into oppositely arranged grooves formed in the sections 2a which make up the disk body 2. In this regard, the side edges of the test strips can be secured to the grooves via a press fit, snap connection, by ultrasonic welding, and even using an adhesive and/or bonded connection. Of course, the invention also contemplates arranging the test strips 2b on the disk body 2 in other ways. The test strips 2b can also be integrally formed with the body 2 and/or the sections 2a which make up the body 2.

Figure 31:
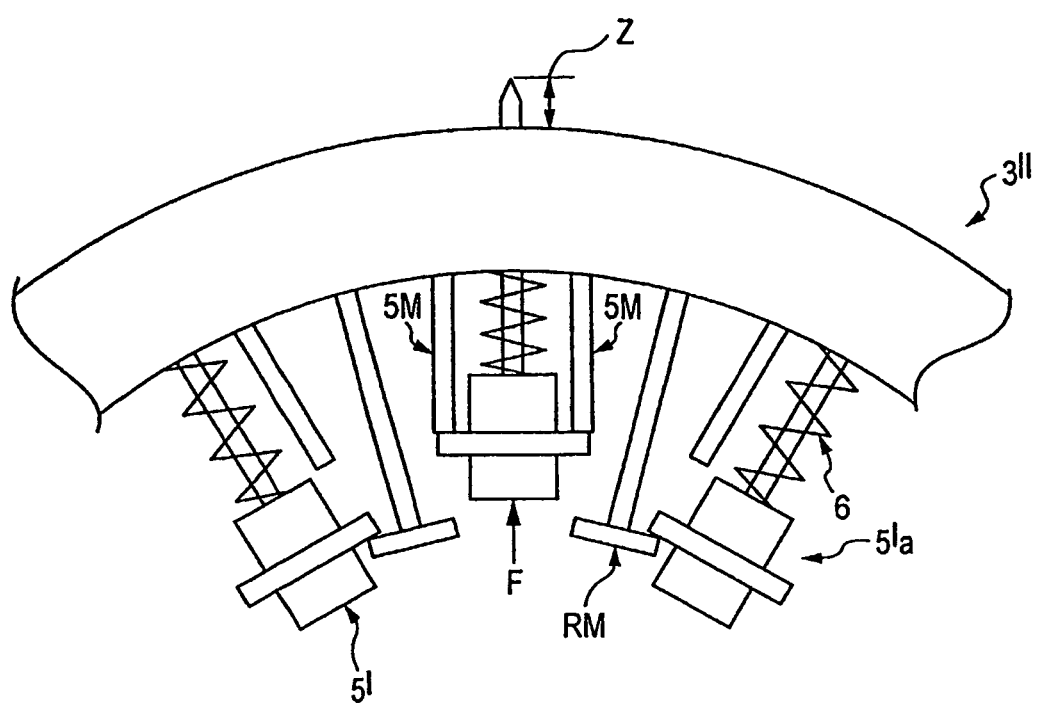
FIG. 31 shows a partial top view of another embodiment of an assembly including a lancet needle holding ring and lancet needles. This arrangement is similar to that of FIG. 26 but additionally includes a plurality of radially oriented stop members which ensure that the lancet needles do not penetrate beyond a predetermined amount.

FIG. 31 illustrates another embodiment of a lancet needle holding ring 3" and needles 5' which can be used on any of the cartridges disclosed herein. The ring 3" is similar to ring 3' shown in FIG. 26 except that it also includes a plurality of lancet needle stop members SM. The stop members SM can be cylindrical wall sections and/or parallel wall members and can be generally radially arranged and equally angularly spaced. Each stop member SM has one end coupled to an inner cylindrical surface of the ring 3" and a free end which engages with portion of a flange of the head 5'a of the lancet needles 5'. This arrangement thus provides for the combination of a plurality of radially oriented retaining members RM which ensure that the lancet needles 5' remain mounted to the lancet needle holding ring 3' when the cartridge is removed from the testing device and the stop members SM which ensure that the lancet needles 5' penetrate a predetermined amount or depth setting "z" when they experience a force F. By manufacturing different cartridges based on their different length stop members SM, a user can select a cartridge based on a desired depth setting "z" from a number of cartridges. It is envisioned that between 2 and 6 cartridge types can be made having different depth settings based on the length of the stop members SM and the user can select one for use on a testing device based on the desired depth setting "z". The retaining members RM and stop member SM can be integrally formed with the ring 3". Of course, this ring 3" and needle 5' arrangement can be used on any of the cartridge embodiments disclosed herein.

Figure 32:
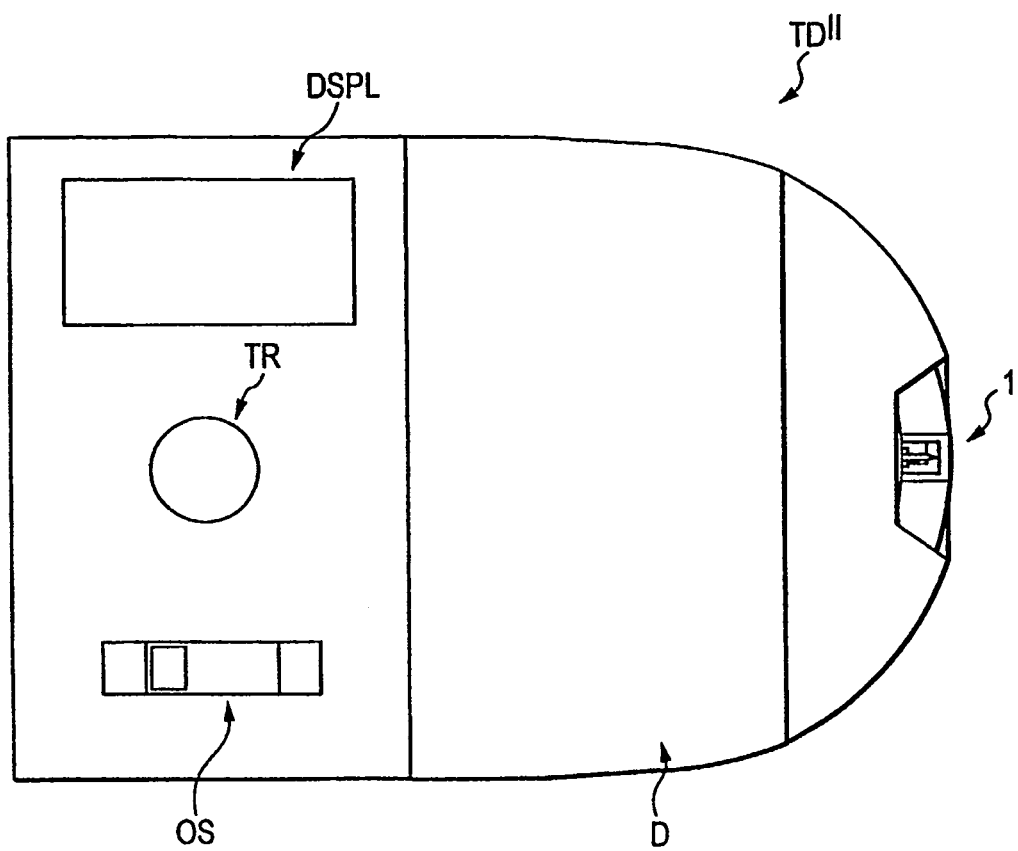
FIG. 32 shows a top view of another embodiment of a testing device. The device is similar to the one shown in FIG. 21, except that the door had been modified to expose less of the cartridge. The test device includes, among other things typically utilized on a test device or glucose meter, a display, a trigger and an on-off switch.

FIG. 32 shows a top view of another embodiment of a testing device TD". The testing device TD" is similar to the one shown in FIG. 21, except that the door D had been modified to expose less of the cartridge 1. The test device TD" includes, among other things typically utilized on a test device or glucose meter, a display DSPL, a trigger TR and an on-off switch OS.

Figure 33:
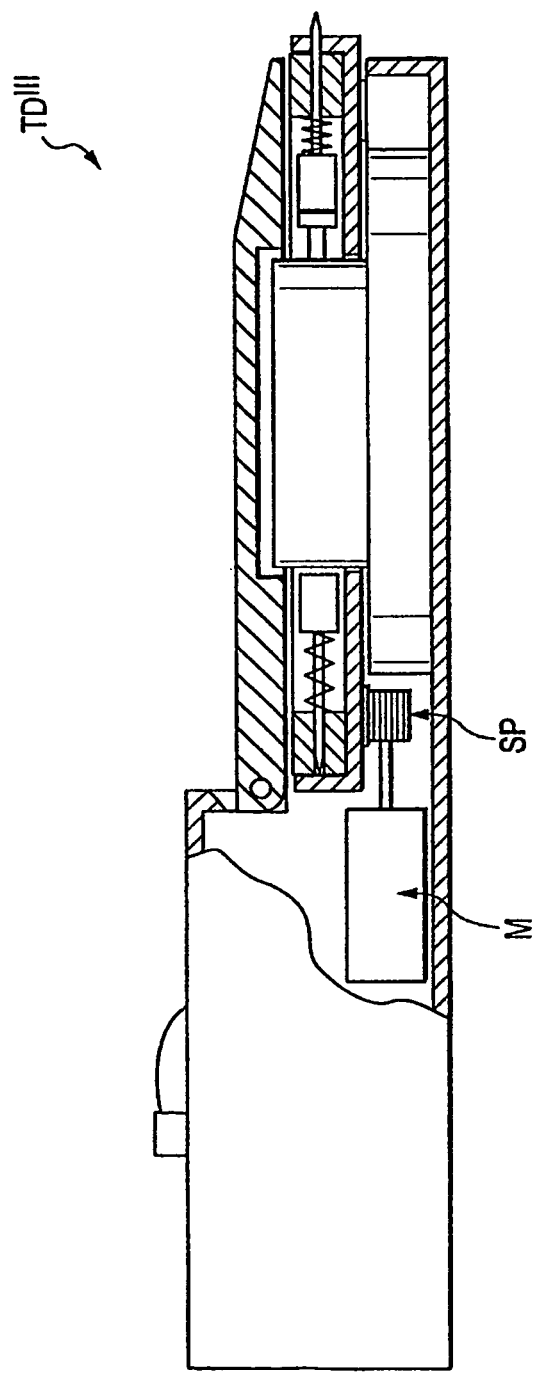
FIG. 33 shows a side view of another embodiment of a testing device. The testing device is similar to the one shown in FIG. 23, except that it utilizes a system for electronically indexing the cartridge between each of the various angular positions, i.e., the cartridge is automatically caused to rotate to the next position once a user receives a testing result. The system uses an electric motor which can be operated by the processor of the testing device and/or switched on by a manual switch. One of the lancet needles is shown in the extended position after the test device has been triggered.

FIG. 33 shows a side view of another embodiment of a testing device $TD^{111}$. The testing device $TD^{111}$ is similar to the one shown in FIG. 23, except that it utilizes a system for electronically indexing the cartridge 1' between each of the various angular positions, i.e., the cartridge 1' is automatically caused to rotate to the next position once a user receives a testing result. The system uses an electric motor M which can be operated by the processor of the testing device $TD^{111}$ and/or switched on by a manual switch. Of course, any type of electric motor can be utilized such as a motor operated electronically. The motor can also be replaced by an actuator such as a linear actuator, a piezoelectric actuator, a linear shape memory alloy (SMA) actuator, or even a magnetic shape memory (MSM) actuator. By way of non-limiting example, once a lancet needle is moved to the extended position after the test device has been triggered and once the testing result is provided, the testing device $TD^{111}$ can execute a time delay of a few second before causing the motor M to index the cartridge 1' to the next position. In order to cause the indexing movement, the motor M uses a sprocket SP which engages with a circular section of radially arranged grooves and teeth arranged on the lower surface of the cartridge F. Of course, this sprocket/tooth engagement can be replaced with any desired high-friction engagement provided that a reliable engagement is provided. Moreover, although the motor M indexing system is shown being utilized with regard to the second cartridge embodiment, such an arrangement can also be utilized with the first cartridge embodiment as well as on any of the testing devices disclosed herein. The benefit of such an indexing system is, of course, that it eliminates the need for the user to manually index the cartridge in the testing device.

Figure 34:
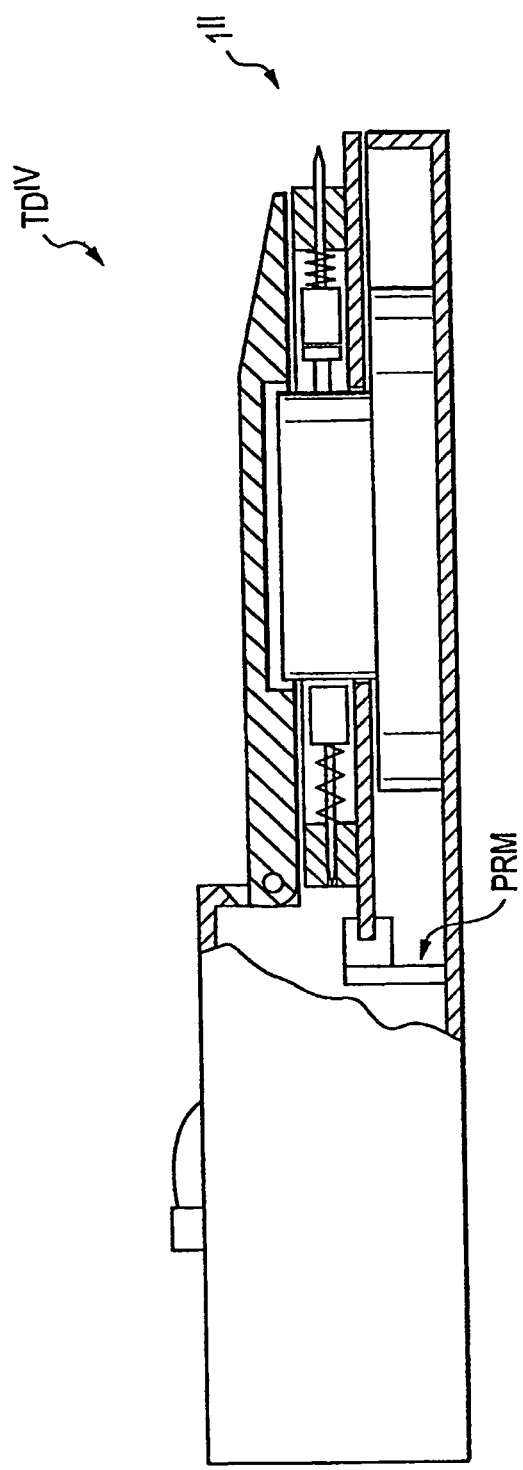
FIG. 34 shows a side view of another embodiment of a testing device. The testing device is similar to the one shown in FIG. 22, except that it utilizes a system for securing the cartridge in each of the various angular positions, i.e., the cartridge is temporarily locked in each of the various positions. The system uses a deflecting position retaining member which engages with each of a plurality of circumferential notches in the cartridge. One of the lancet needles is shown in the extended position after the test device has been triggered.
Figure 35:
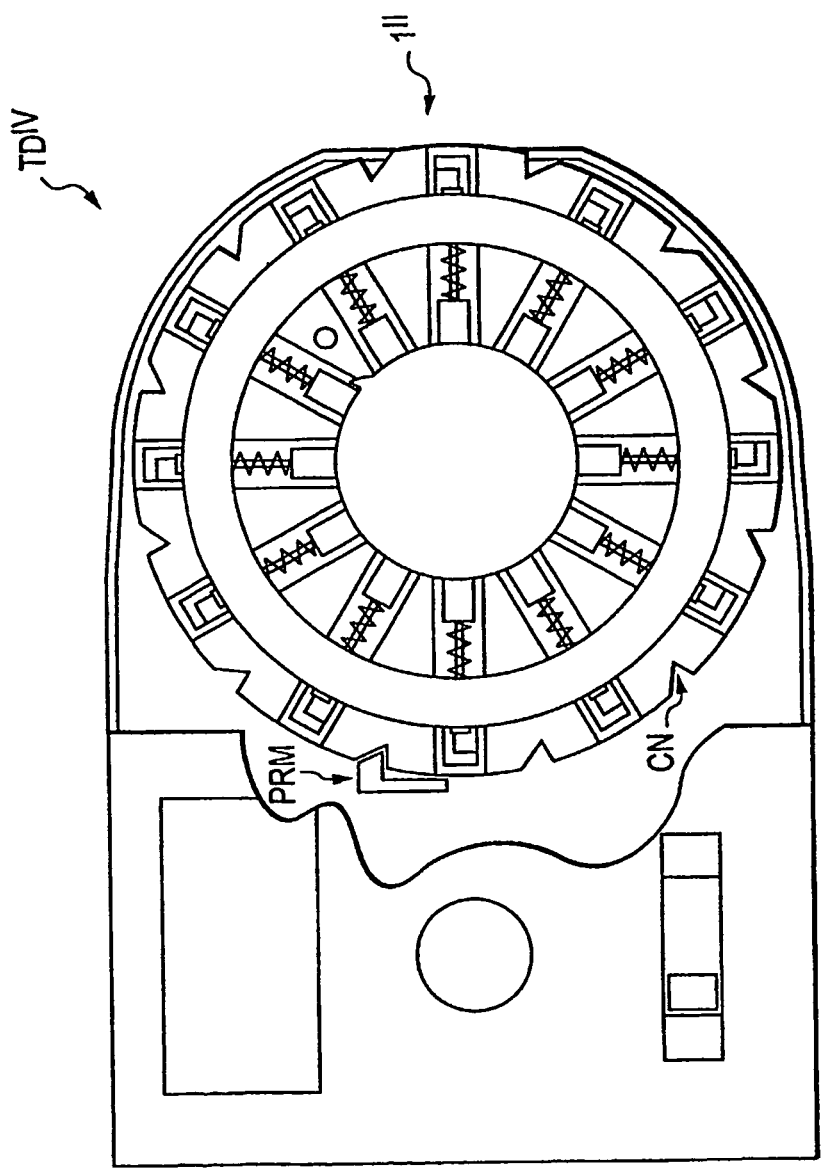
FIG. 35 shows a top view of the testing device of FIG. 34. The Figure shows the position retaining member engaging with one of the plurality of circumferential notches of the cartridge.
Figure 36:
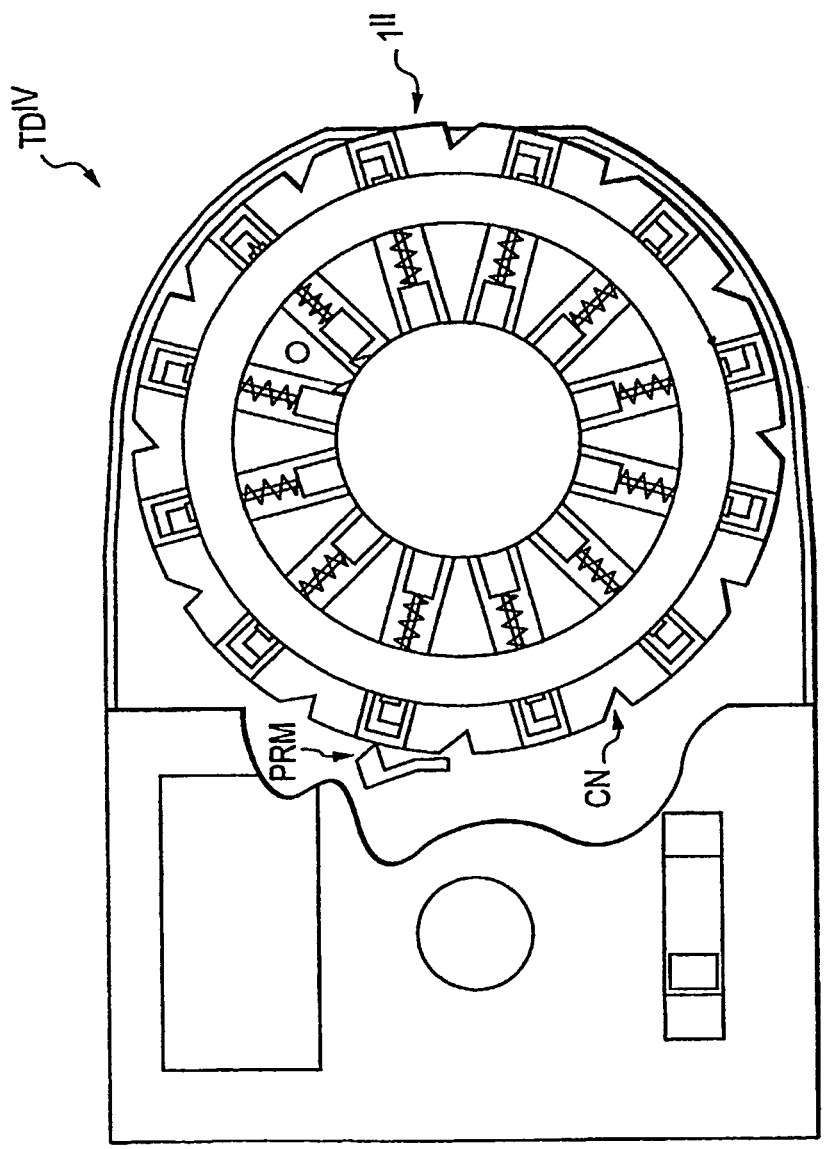
FIG. 36 shows another top view of the testing device of FIG. 34. The Figure shows the position retaining member being deflected as the cartridge is moved to another position wherein it will engage with one of the plurality of circumferential notches of the cartridge. The Figure also shows how the alignment projection of the mounting arrangement engages with the lancet needles as the cartridge is rotated.

FIGS. 34-36 show another embodiment of a testing device $TD^{IV}$ and a third embodiment of the cartridge 1". The testing device $TD^{IV}$ is similar to the one shown in FIG. 22, except that it utilizes a system for securing the cartridge 1" in each of the various angular positions, i.e., the cartridge 1" is temporarily locked in each of the various positions. The system uses a deflecting position retaining member PRM which engages with each of a plurality of circumferential notches CN in the cartridge 1". The member PRM has one end which is coupled to a wall of the testing device housing and a free end which releasably engages with each of the notches CN. The arrangement is such that when the member PRM engages with one of the notches CN, the lancet needle and test strip are properly aligned and ready to be used (see FIG. 35). FIG. 36 shows the position retaining member PRM being deflected as the cartridge 1" is moved to another position wherein it will engage with one of the plurality of circumferential notches CN of the cartridge 1". The design of the notches CN is such that they prevent the cartridge 1" from being rotated clockwise, i.e., they also serve as a one-way rotation mechanism. Of course, this indexing arrangement can be used on any of the cartridges and testing devices disclosed herein including one which also utilizes the indexing motor M of FIG. 33.

Figure 37:
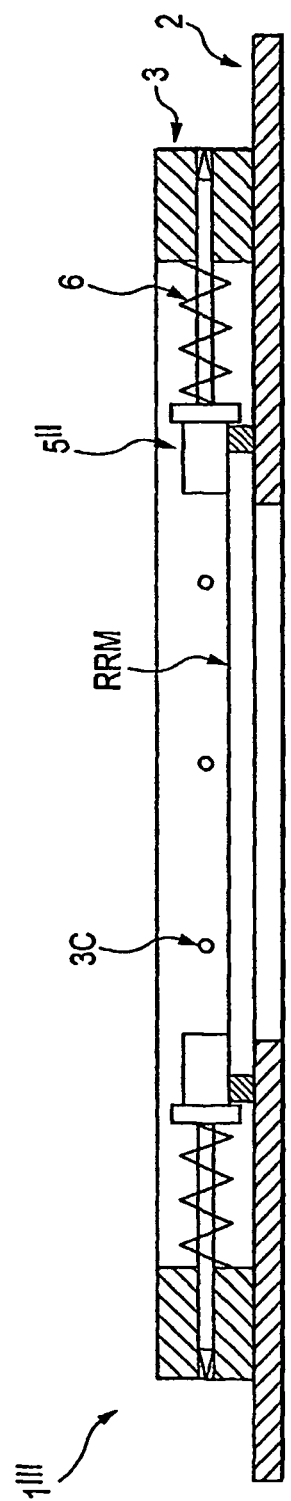
FIG. 37 shows a cross-section view of another embodiment of an assembly including a lancet needle holding ring and lancet needles. This arrangement provides for a retaining ring member which ensures that the lancet needles remain mounted to the lancet needle holding ring. The cartridge can be used on any of the testing devices shown in FIGS. 9-22, 32 and 34-36. The retaining ring member and lancet needles can also be used on the cartridges shown in FIGS. 23-25 and 33.

FIG. 37 shows a cross-section view of another embodiment of an assembly, i.e., a cartridge $1^{111}$ which includes a lancet needle holding ring 3 and lancet needles 5". This arrangement provides for a generally circular retaining ring member RRM which ensures that the lancet needles 5" remain mounted to the lancet needle holding ring 3. The lancet needles 5" are similar to those of FIGS. 5a-c except that they include a circular flange which engages with the member RRM. The ring RRM can, in particular, be used in place of the retaining members RM shown in FIGS. 26 and 31. The cartridge 1$^{111}$ can be used on any of the testing devices shown in FIGS. 9-22, 32 and 34-36. The retaining ring member RRM and lancet needles 5'' can also be used on the cartridges shown in FIGS. 23-25 and 33.

Figure 38:
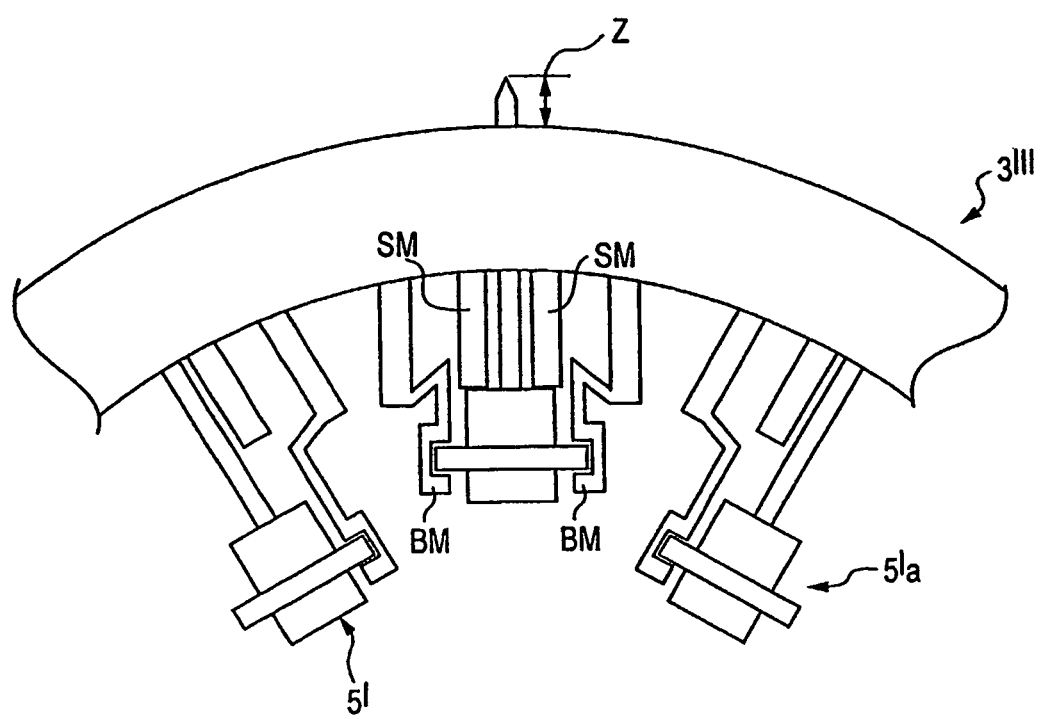
FIG. 38 shows a partial top view of another embodiment of an assembly including a lancet needle holding ring and lancet needles. This arrangement is similar to that of FIG. 26 but additionally includes a plurality of radially oriented stop members which ensure that the lancet needles do not penetrate beyond a predetermined amount and biasing members in place of the lancet needle springs.

FIG. 38 illustrates another embodiment of a lancet needle holding ring 3$^{111}$ and needles 5' which can be used on any of the cartridges disclosed herein. The ring 3$^{111}$ is similar to ring 3' shown in FIG. 26 except that it also includes a plurality of lancet needle stop members SM and, in place of the springs 6, biasing members BM are used to bias the lancet needles towards a resting and/or initial position. The stop members SM can be cylindrical wall sections and/or parallel wall members and can be generally radially arranged and equally angularly spaced. Each stop member SM has one end coupled to an inner cylindrical surface of the ring 3$^{111}$ and a free end which engages with portion of a flange of the head 5'$a$ of the lancet needles 5'. This arrangement thus provides for the combination of a plurality of radially oriented biasing members BM which ensure that the lancet needles 5' remain mounted to the lancet needle holding ring 3$^{111}$ when the cartridge is removed from the testing device and the stop members SM which ensure that the lancet needles 5' penetrate a predetermined amount or depth setting "z". By manufacturing different cartridges based on their different length stop members SM, a user can select a cartridge based on a desired depth setting "z" from a number of cartridges. It is envisioned that between 2 and 6 cartridge types can be made having different depth settings based on the length of the stop members SM and the user can select one for use on a testing device based on the desired depth setting "z". The biasing members BM and stop member SM can be integrally formed with the ring 3$^{111}$. Of course, this ring 3$^{111}$ and needle 5' arrangement can be used on any of the cartridge embodiments disclosed herein.

The testing devices can preferably made transparent and/or translucent so that a user will clearly be able to identify when and how much of the cartridge has already been utilized. Of course, the invention is not limited to a body design which is transparent and/or translucent.

The operation of a testing device using a cartridge of the type described herein will now be explained with reference to the embodiment shown in FIGS. 19-22. As an initial step, the user will open the door D and install the cartridge 1 onto the mounting arrangement MA. This is accomplished by aligning the notch 8 with the projection 108. The user can then force the cartridge 1 downwards until the bottom surface of the disk 2 contacts the surface 105. The user can then close the door D and begin using the device by switching on the testing device TD, placing a finger FNG in the position shown in FIG. 22, and triggering the testing device TD to cause one of the lancet needles to puncture the finger FNG. The user will then rotate the finger to place a blood drop on the exposed end of the test strip. At this point, the device can function to automatically provide a test result after triggering and sensing the blood drop on the test strip, or upon the user manually inputting a request for testing by, e.g., pushing the trigger TR a second time to activate the testing procedure. Once the user has received a result, the user can then manually rotate the cartridge 1 by, e.g., applying a rubbing force on the edge OE, or as is preferred, by activating the indexing motor M. This activation can occur automatically (i.e., after a time delay) or by, e.g., the user pressing the trigger button TR a third time. The device will then be ready for use again at a later time and/or by a different user.

It is also possible to provide a number or letter on each test strip of the cartridge so that a user will be able to see which test strip is being utilized and how many remain for use. The testing device can also be provided with a system which senses the position of the cartridge and indicates the position number digitally. By way of non-limiting example, this can be accomplished using a bar-code reader system. All the parts of the cartridge, with the exception of the springs 6 and needles (which can respectively be made of spring steel and stainless steel), may be made from plastic materials and can be formed using conventional injection molding techniques or other known manufacturing methods. However, when practical, other materials and manufacturing processes may also be utilized.

It is noted that the foregoing examples have been provided merely for the purpose of explanation and are in no way to be construed as limiting of the present invention. While the present invention has been described with reference to an exemplary embodiment, it is understood that the words which have been used herein are words of description and illustration, rather than words of limitation. Changes may be made, within the purview of the appended claims, as presently stated and as amended, without departing from the scope and spirit of the present invention in its aspects. Although the present invention has been described herein with reference to particular means, materials and embodiments, the present invention is not intended to be limited to the particulars disclosed herein; rather, the present invention extends to all functionally equivalent structures, methods and uses, such as are within the scope of the appended claims.

What is claimed is:

1. A combination comprising:
    a rotatably mountable cartridge comprising:
        a plurality of lancet needles each comprising a needle portion that is radially oriented;
        a plurality of test strips each comprising electrical contacts having portions structured and arranged to be exposed to a user's blood drop; and
    a testing device comprising:
        a cartridge receiving area; and
        a testing area visible and accessible from outside the testing device,
    wherein, when the cartridge is installed on the testing device while resting on a horizontal surface, the portions of the electrical contracts exposed to a user's blood drop extend into the testing area and are visible and accessible to a user from a position above the testing device.

2. The combination of claim 1, wherein each of the plurality of test strips is generally radially oriented.

3. The combination of claim 1, wherein each of the plurality of lancet needles is movably mounted to a disk-shaped body.

4. The combination of claim 1, wherein each of the plurality of test strips is non-movably mounted to a disk-shaped body.

5. The combination of claim 1, wherein the cartridge has an outer diameter of no greater than about 2 inches.

6. The combination of claim 1, wherein the cartridge has a thickness of no greater than about 0.25 inches.

7. The combination of claim 1, further comprising a plurality of springs, wherein each spring is mounted to one of the plurality of lancet needles.

8. The combination of claim 1, wherein each of the plurality of lancet needles comprises a head portion.

9. The combination of claim 1, further comprising a ring-shaped member arranged on the cartridge, wherein each needle portion is arranged within an opening of the ring-shaped member.

10. A method of puncturing a surface of skin using the combination of claim 1, the method comprising:
    placing a finger in the visible and accessible testing area;
    triggering the testing device so that one of the plurality of lancet needles is caused to penetrate the user's skin; and
    placing an amount of blood on one of the plurality of test strips.

11. A testing device comprising:
    a housing; and
    a generally disk-shaped cartridge comprising a plurality of lancet needles and a plurality of test strips,
    said cartridge being capable of being removably and rotatably mounted within the housing,
    wherein the housing has a testing area that is visible and accessible to a user such that, when the cartridge is installed in the housing and when the testing device is resting on a horizontal surface, portions of electrical contacts of one of the test strips are exposed to a user's blood drop and extend into the testing area so as to be visible and accessible from a position above the testing device.

12. A combination comprising:
    a generally circular cartridge comprising:
        an outer circumference;
        a plurality of test strips each comprising electrical contacts having portions structured and arranged to be exposed to a user's blood drop;
    a testing device comprising:
        a cartridge receiving area; and
        a testing area arranged outside a housing of the testing device;
    wherein, when the cartridge is installed on the testing device while resting on a horizontal surface, at least one of:
        a portion of the outer circumference extends outside the housing and portions of electrical contacts are exposed, accessible and visible from outside the testing device; and
        portions of electrical contacts extend into the testing area and are each accessible to a user an visible from a position above the testing device.

* * * * *